(12) United States Patent
Odle et al.

(10) Patent No.: US 10,048,199 B1
(45) Date of Patent: Aug. 14, 2018

(54) METROLOGY SYSTEM FOR AN EXTREME ULTRAVIOLET LIGHT SOURCE

(71) Applicant: ASML Netherlands B.V., Veldhoven (NL)

(72) Inventors: Jesse Quinn Odle, San Diego, CA (US); Jason Michael Arcand, Escondido, CA (US)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/463,909

(22) Filed: Mar. 20, 2017

(51) Int. Cl.
   *G01N 21/21* (2006.01)
   *G01N 21/55* (2014.01)
   *H05G 2/00* (2006.01)

(52) U.S. Cl.
   CPC ............ *G01N 21/55* (2013.01); *G01N 21/21* (2013.01); *H05G 2/008* (2013.01); *G01N 2201/068* (2013.01); *G01N 2201/0691* (2013.01); *G01N 2201/0697* (2013.01); *G01N 2201/06113* (2013.01)

(58) Field of Classification Search
   CPC .. H05G 2/008; H05G 2/005; G01N 2021/653; G01N 21/65; G01N 2201/06113
   See application file for complete search history.

(56) References Cited

U.S. PATENT DOCUMENTS

| | | | |
|---|---|---|---|
| 8,604,452 B2 * | 12/2013 | Ershov | G03F 7/70033 250/493.1 |
| 8,648,999 B2 | 2/2014 | Graham et al. | |
| 9,000,405 B2 | 4/2015 | Fleurov et al. | |
| 9,055,657 B2 * | 6/2015 | Hori | G21K 5/04 |
| 9,516,732 B2 * | 12/2016 | Wagner | H01S 3/2316 |
| 9,735,535 B2 * | 8/2017 | Ershov | H01S 3/105 |
| 2004/0105095 A1 | 6/2004 | Stobrawa et al. | |
| 2004/0195529 A1 | 10/2004 | Hergenhan et al. | |
| 2006/0215712 A1 * | 9/2006 | Ziener | H05G 2/003 372/2 |
| 2007/0272669 A1 | 11/2007 | Comley et al. | |
| 2008/0087847 A1 * | 4/2008 | Bykanov | H05G 2/003 250/504 R |
| 2009/0161201 A1 * | 6/2009 | Ershov | G03F 7/70033 359/333 |
| 2010/0117009 A1 | 5/2010 | Moriya et al. | |
| 2010/0140512 A1 | 6/2010 | Suganuma et al. | |
| 2011/0317256 A1 * | 12/2011 | Hou | H01S 3/076 359/337.21 |

(Continued)

OTHER PUBLICATIONS

Harry C. Kim, U.S. International Searching Authority, International Search Report and Written Opinion, counterpart PCT Application No. PCT/US2018/018422, dated Mar. 12, 2018, 11 pages total.

*Primary Examiner* — Marcus Taningco
(74) *Attorney, Agent, or Firm* — DiBerardino McGovern IP Group LLC

(57) ABSTRACT

A system for an EUV light source includes a metrology light source configured to emit a metrology light beam; and an optical beam combiner positioned to receive the metrology light beam and at least one other light beam and to direct the metrology light beam and the at least one other light beam onto a beam path toward a target region. After interacting with the optical beam combiner, the metrology light beam and the at least one other light beam have the same polarization state.

34 Claims, 14 Drawing Sheets

(56) References Cited

U.S. PATENT DOCUMENTS

| | | | |
|---|---|---|---|
| 2012/0012762 A1* | 1/2012 | Nowak | B82Y 20/00 250/504 R |
| 2012/0080584 A1* | 4/2012 | Partlo | G03F 7/70033 250/214.1 |
| 2012/0146507 A1* | 6/2012 | Yanagida | H05G 2/003 315/111.01 |
| 2013/0322482 A1* | 12/2013 | Sandstrom | H01S 3/08 372/50.11 |
| 2014/0072006 A1 | 3/2014 | Sandstrom | |
| 2015/0001408 A1* | 1/2015 | Frank | G02B 26/0833 250/372 |
| 2015/0041659 A1 | 2/2015 | Graham et al. | |
| 2015/0102239 A1* | 4/2015 | Yanagida | H05G 2/005 250/504 R |
| 2016/0198557 A1* | 7/2016 | Enzmann | H05G 2/008 250/504 R |
| 2016/0290928 A1 | 10/2016 | Krishnamachari et al. | |

* cited by examiner

METROLOGY SYSTEM FOR AN EXTREME ULTRAVIOLET LIGHT SOURCE

TECHNICAL FIELD

This disclosure relates to a metrology system for an extreme ultraviolet light source.

BACKGROUND

Extreme ultraviolet ("EUV") light, for example, electromagnetic radiation having wavelengths of around 50 nm or less (also sometimes referred to as soft x-rays), and including light at a wavelength of about 13 nm, may be used in photolithography processes to produce extremely small features in substrates, for example, silicon wafers.

Methods to produce EUV light include, but are not necessarily limited to, converting a material that has an element, for example, xenon, lithium, or tin, with an emission line in the EUV range in a plasma state. In one such method, often termed laser produced plasma ("LPP"), the required plasma may be produced by irradiating a target material, for example, in the form of a droplet, plate, tape, stream, or cluster of material, with an amplified light beam that may be referred to as a drive laser. For this process, the plasma is typically produced in a sealed vessel, for example, a vacuum chamber, and monitored using various types of metrology equipment.

SUMMARY

In one general aspect, a system for an EUV light source includes a metrology light source configured to emit a metrology light beam; and an optical beam combiner positioned to receive the metrology light beam and at least one other light beam and to direct the metrology light beam and the at least one other light beam onto a beam path toward a target region. After interacting with the optical beam combiner, the metrology light beam and the at least one other light beam have the same polarization state.

Implementations may include one or more of the following features. The optical beam combiner may include a polarizing beam splitter, and an optical modulator, and the system for the EUV light source also may include a control system coupled to the optical modulator, the control system configured to control the optical modulator such that the metrology light beam and the at least one other light beam have the same polarization state after passing through the optical modulator toward the target region. The metrology light beam and the at least one other light beam may include substantially the same spectral content, and the metrology light beam and the at least one other light beam may have different polarization states prior to passing through the optical modulator of the optical beam combiner.

The at least one other light beam may include a first light beam, the metrology light beam may have a first spectral content, and the first light beam may have a second spectral content, the first spectral content including at least a first wavelength and the second spectral content including at least a second wavelength, the first and second wavelengths being different wavelengths, and the optical beam combiner may include a dichroic optical element, the dichroic optical element configured to transmit light having one of the first wavelength and the second wavelength and to reflect light having the other of the first wavelength and the second wavelength.

The system also may include a second optical element, the second optical element being between the optical modulator and the target region, and the second optical element may be configured to direct a reflection of the metrology light beam and a reflection of the at least one other beam onto a detection beam path. The system also may include a polarization-based optical isolator on the detection path between at least one of the one or more sensors and the second optical element, the polarization-based optical isolator including: a second optical modulator coupled to the control system; and a third optical element configured to interact with incident light based on a polarization state of the incident light, where the optical modulator of the polarization-based optical isolator is configured to be controlled such that, after passing through the optical modulator, a polarization state of a reflection of the metrology light beam and a polarization state of a reflection of the first light beam are different. Each of the optical modulator and the second optical modulator may include an electro-optic modulator; and the first optical component, the second optical component, and the third optical component each may include a polarizing beam splitter, the third optical element being positioned to deflect a reflection of the first light beam away from the detection path.

The system may include a beam conditioning module between the metrology light source and the optical beam combiner, the beam conditioning module including one or more optical elements configured to increase a beam diameter of the metrology light beam.

The at least one other light beam may be a first light beam having an energy sufficient to modify a geometric distribution of target material in an initial target that interacts with the first light beam.

The system also may include one or more sensors, each positioned to receive a portion of a light beam that propagates on the detection beam path. The one or more sensors may include a first sensor configured to accumulate light over a first time period and a second sensor configured to monitor changes in an amount of light received at instances within the first time period. The first sensor may include a camera and the second sensor includes a photodiode.

The metrology light source may be configured to emit a continuous wave light beam.

The metrology light source may be controllable to emit either a pulsed light beam or a continuous wave light beam.

In another general aspect, a method for an EUV light source includes directing a metrology light beam onto a beam path toward an initial target region configured to receive a target, the metrology light beam having a wavelength and a polarization state, and the target including target material, the target material including material that reflects light having the wavelength of the metrology light beam and emits EUV light when in a plasma state; directing a first light beam onto the beam path toward the initial target region, the first light beam and the metrology light beam having substantially the same polarization state, and the first light beam having an energy sufficient to alter a geometric distribution of target material in the target to form a modified target; and directing a second light beam toward a modified target region that receives the modified target, the second light beam having an energy sufficient to convert at least some of the target material in the modified target to plasma that emits EUV light.

Implementations may include one or more of the following features. A reflection of the metrology light beam may be received, and the first light beam may be directed onto the beam path toward the target region based on the received reflection of the metrology light beam. The first light beam may be generated by a first light source, and the first light beam being directed on the beam path toward the target region based on the received reflection may include the first light source being controlled to emit the first light beam only after the reflection of the metrology light beam is received.

Directing the metrology light beam onto the beam path toward the initial target region may include passing the metrology light beam through an electro-optic modulator, directing the first light beam onto the beam path toward the initial target region may include passing the first light beam through the electro-optic modulator, and the electro-optic modulator is controlled such that, after passing through the electro-optic modulator, the metrology light beam and the first light beam have the same polarization state. In some implementations, prior to directing the metrology light beam and the first light beam onto the beam path, a direction of propagation of at least one of the metrology light beam and the first light beam is changed such that both the metrology light beam and the first light beam propagate toward the initial target region. The direction of propagation of the at least one of the metrology light beam and the first light beam may be changed through interaction with a polarizing beam splitter. Prior to passing through the electro-optic modulator, the metrology light beam and the first light beam may have different polarization states.

A beam diameter of the metrology light beam directed toward the initial target region may be larger than a beam diameter of the first light beam directed toward the initial target region. The metrology light beam may interact with a beam conditioning system prior to directing the metrology light beam toward the initial target region, the beam conditioning system expanding a diameter of the metrology light beam to at least the diameter of the initial target region.

The metrology light beam directed on the beam path and the first light beam directed on the beam path may have substantially the same spectral content.

In another general aspect, light associated with a metrology light beam from an interior of a vacuum chamber of an EUV light source is received, at an imaging device; light associated with a first light beam from the interior of the vacuum chamber is received at the imaging device. The first light beam has an energy sufficient to modify a geometric distribution of target material in a target in the vacuum chamber, and the light associated with the first light beam is received at a different portion of the imaging device than the light associated with the metrology light beam and at a different time than the light associated with the metrology light beam. A representation of the metrology light beam and the first light beam in the vacuum chamber is generated based on the received light associated with the metrology light beam and the received light associated with the first light beam, the representation including two-dimensional spatial information related to the metrology light beam and the first light beam in the vacuum chamber.

Implementations may include one or more of the following features. Light associated with a second light beam from the vacuum chamber may be received at the imaging device, the second light beam having an energy sufficient to convert target material to EUV light when in a plasma state, and the representation also may include a representation of the second light beam in the vacuum chamber based on the received light associated with the second light beam, and the representation further includes two-dimensional spatial information related to the second light beam in the vacuum chamber. The light associated with the metrology light beam may include a reflection of the metrology light beam from target material in the vacuum chamber, the light associated with the first light beam may include a reflection of the first light beam from the target material in the vacuum chamber, and the light associated with the second light beam may include non-EUV light emitted by a plasma formed by an interaction between the second light beam and the target material in the vacuum chamber. The light associated with the metrology light beam is received at the imaging device at a first time; the light associated with the first light beam is received at the imaging device at a second time; the light associated with the second light beam at the imaging device at a third time; and determining spatial coordinates for the representation of the metrology light beam, the representation of the first light beam, and the representation of the second light beam based on the first time, the second time, and the third time, respectively. The first time, the second time, and the third times may be different times. The spatial coordinates may correspond to spatial coordinates in the vacuum chamber. The spatial coordinates may represent a location in the vacuum chamber in a first dimension and a second dimension, the first dimension being along a direction that is parallel to a direction in which target material is introduced into the vacuum chamber, and the second dimension being orthogonal to the first dimension. The representation may be analyzed to determine an estimated value of one or more properties of the first light beam in the vacuum chamber. Analyzing the representation includes may include a centroid of the two-dimensional spatial information related to the first light beam to determine an estimate of a position of the first light beam in the vacuum chamber.

In some implementations, the generated representation is visually presented, the presented representation including a first display style associated with the metrology light beam, a second display style associated with the first light beam, and a third display style associated with the second light beam, the first display style, the second display style, and the third display style being visually distinguishable from each other.

Implementations of any of the techniques described above may include an EUV light source, a system, a method, a process, a device, or an apparatus. The details of one or more implementations are set forth in the accompanying drawings and the description below. Other features will be apparent from the description and drawings, and from the claims.

DRAWING DESCRIPTION

Figure 3A:
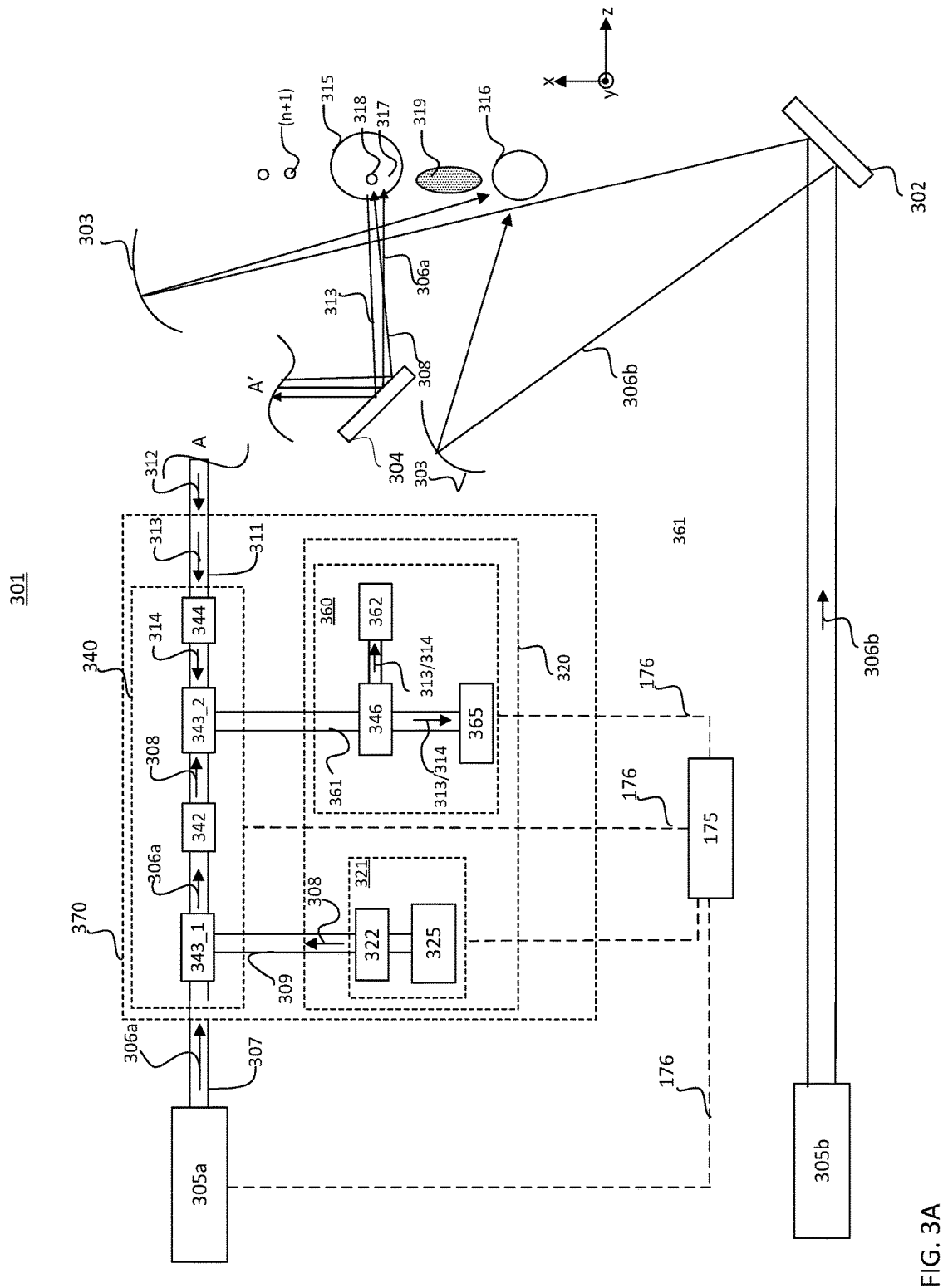
FIG. 3A is a block diagram of an example of an EUV light source.
Figure 3D:
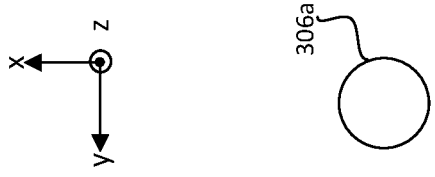
Figure 3C:
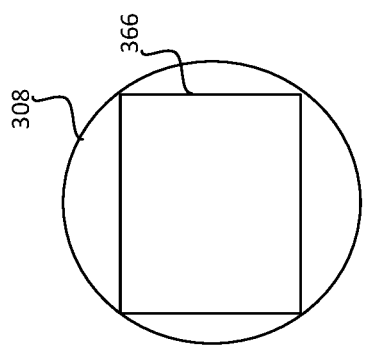
Figure 3B:

FIGS. 3B, 3C, and 3D illustrate a target, a metrology light beam, and a light beam, respectively, at a target region in the EUV light source of FIG. 3A.

Figure 3E:
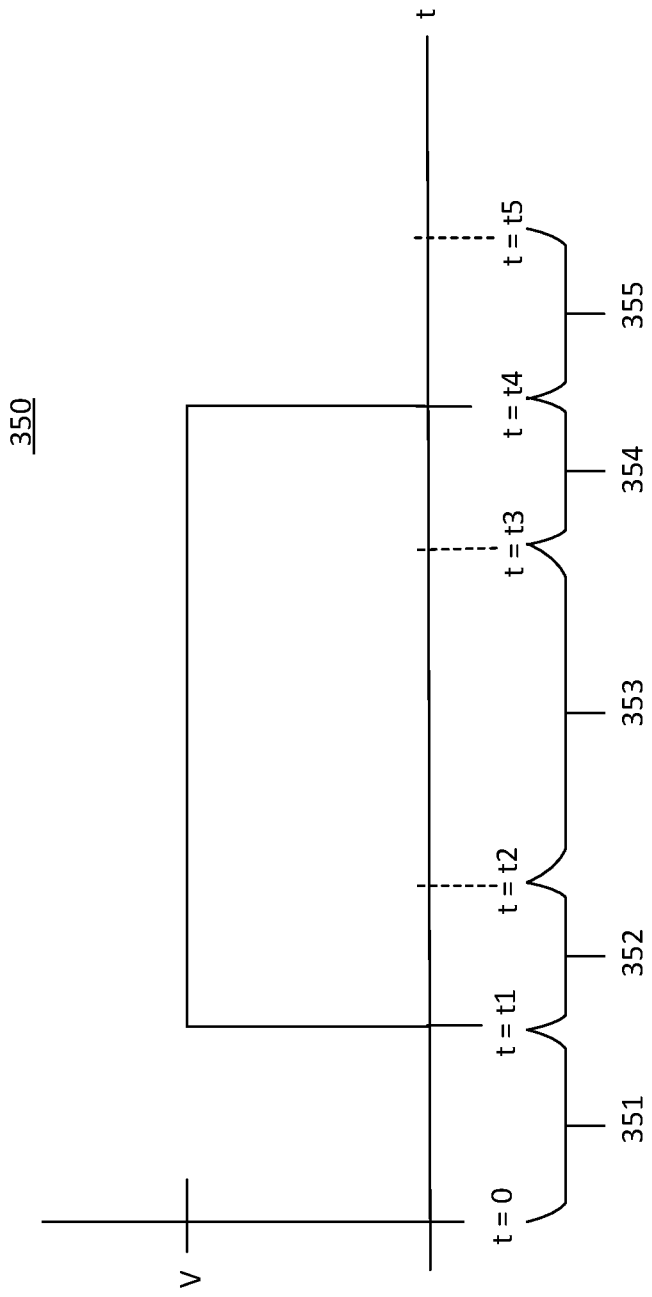

FIG. 3E is an example of a timing diagram for an electro-optic modulator used in the EUV light source of FIG. 3A.

Figure 4A:
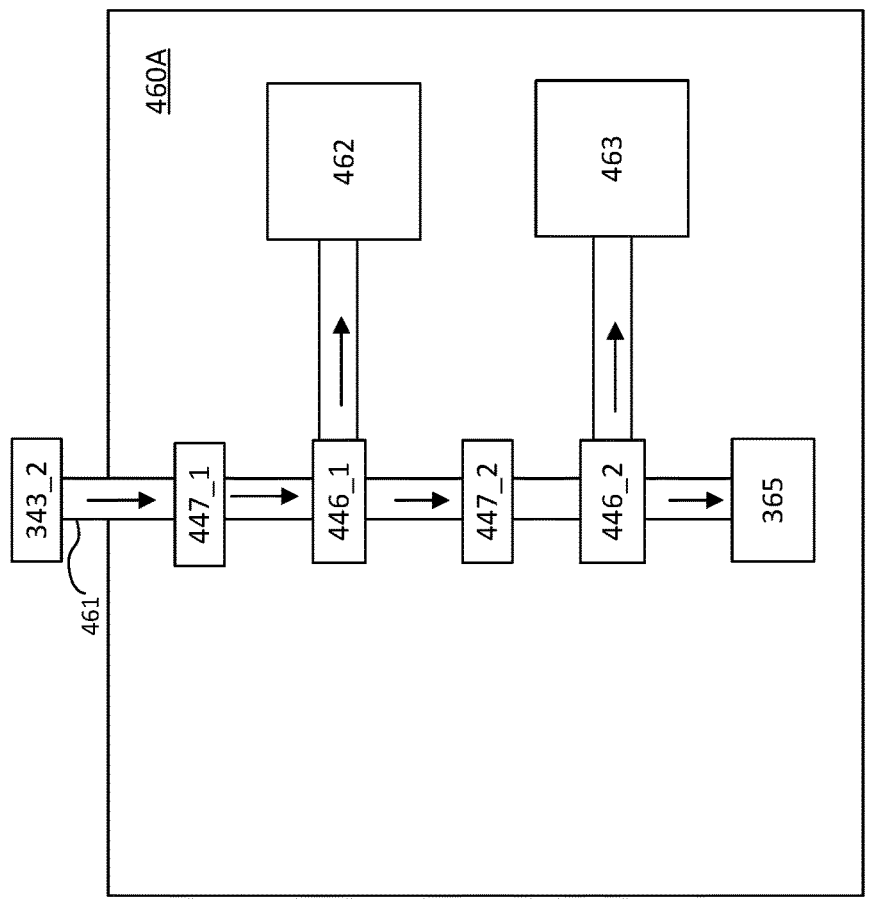
Figure 4B:
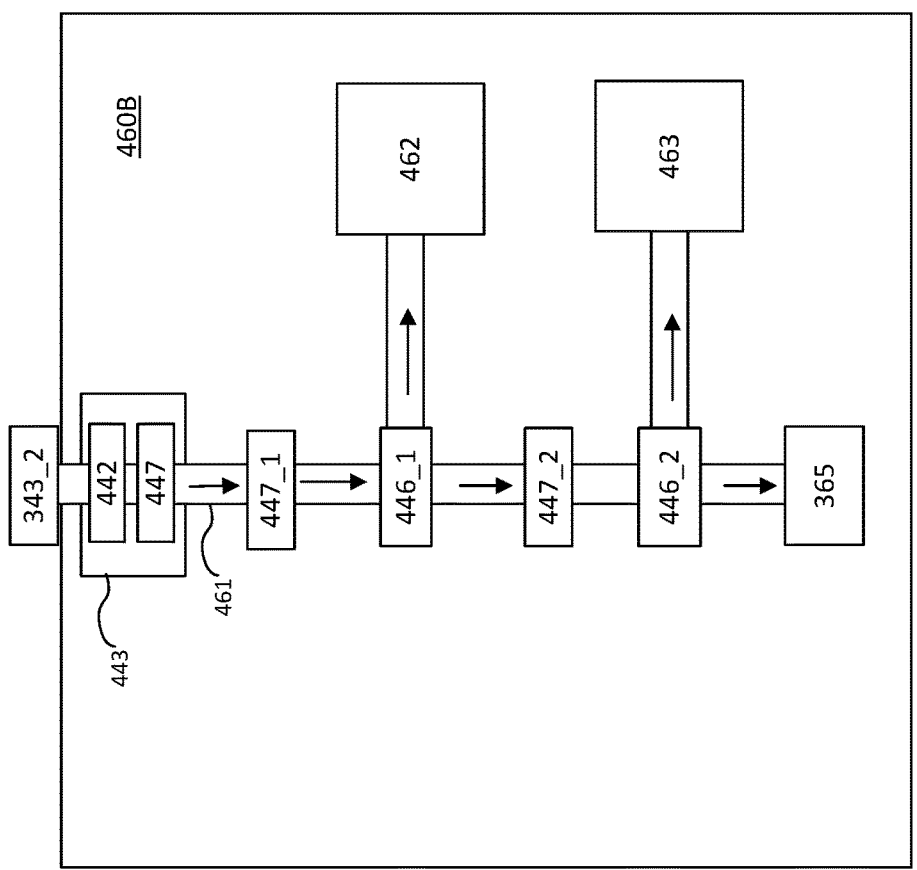

FIGS. 4A and 4B are block diagrams of implementations of detection systems for a metrology system.

Figure 5:
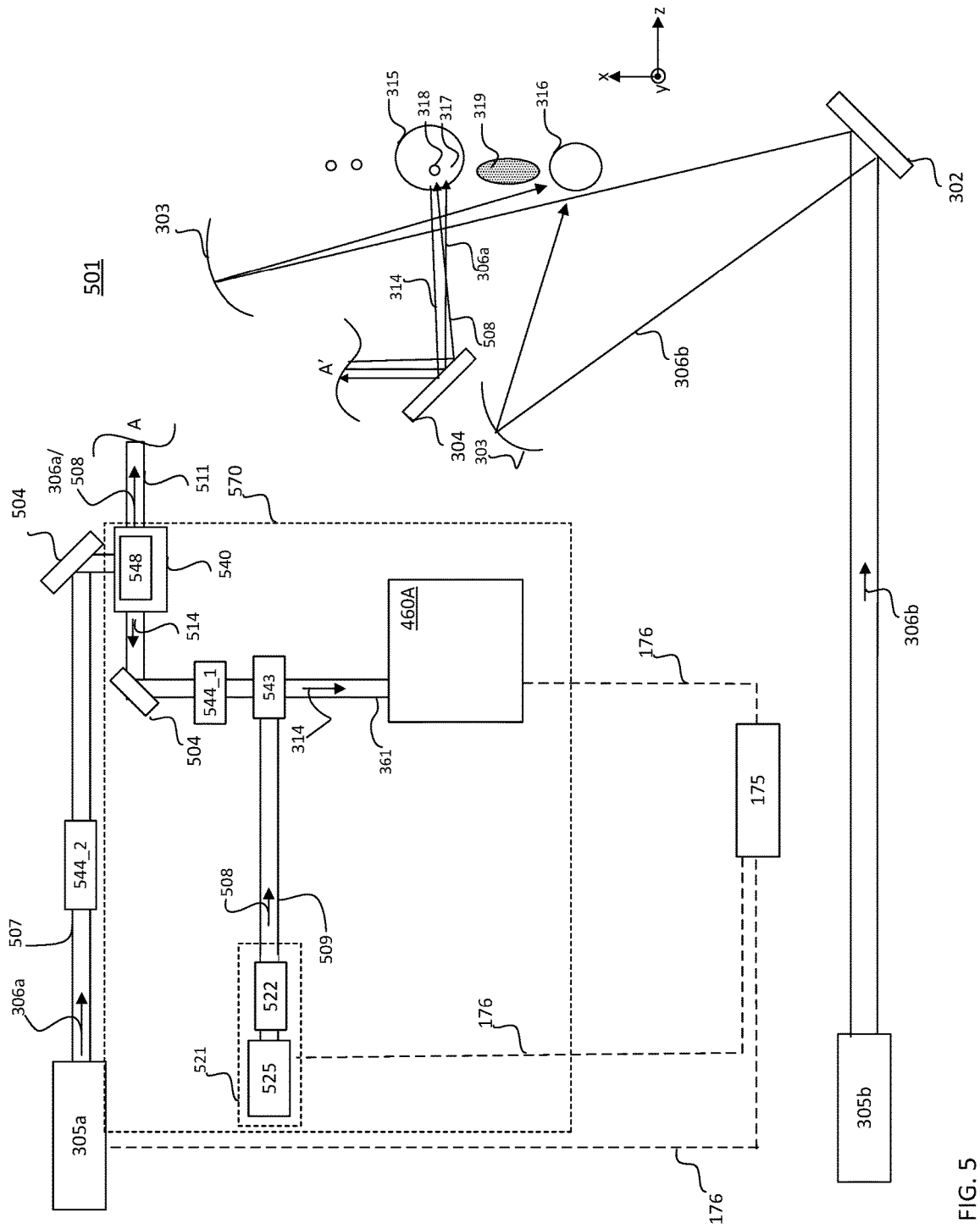

FIG. 5 is a block diagram of an example of an EUV light source.

Figure 6:
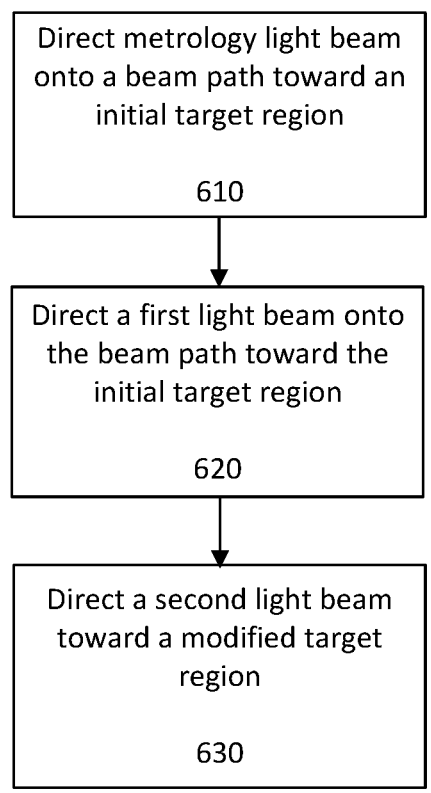

FIG. 6 is a flow chart of an example of a process for using a metrology system in an EUV light source.

Figure 7:
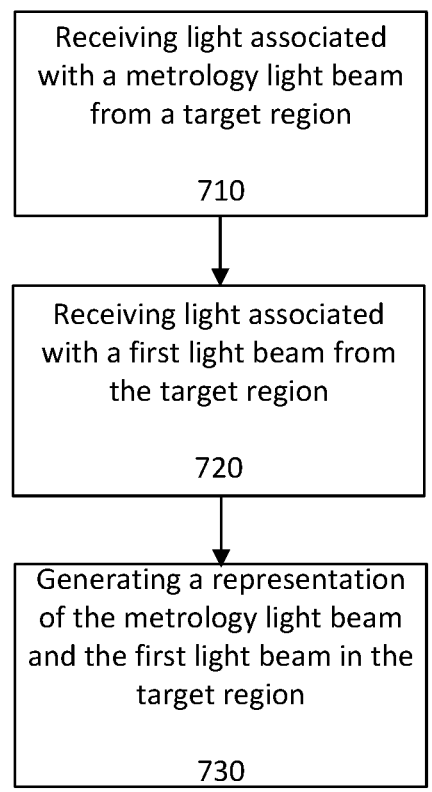

FIG. 7 is a flow chart of an example of a process for generating a representation of a target region in a vacuum vessel of an EUV light source.

FIGS. 8A, 8B, and 9A-9C are examples of representations produced by a process such as the process shown in the flow chart of FIG. 7.

Figure 10A:
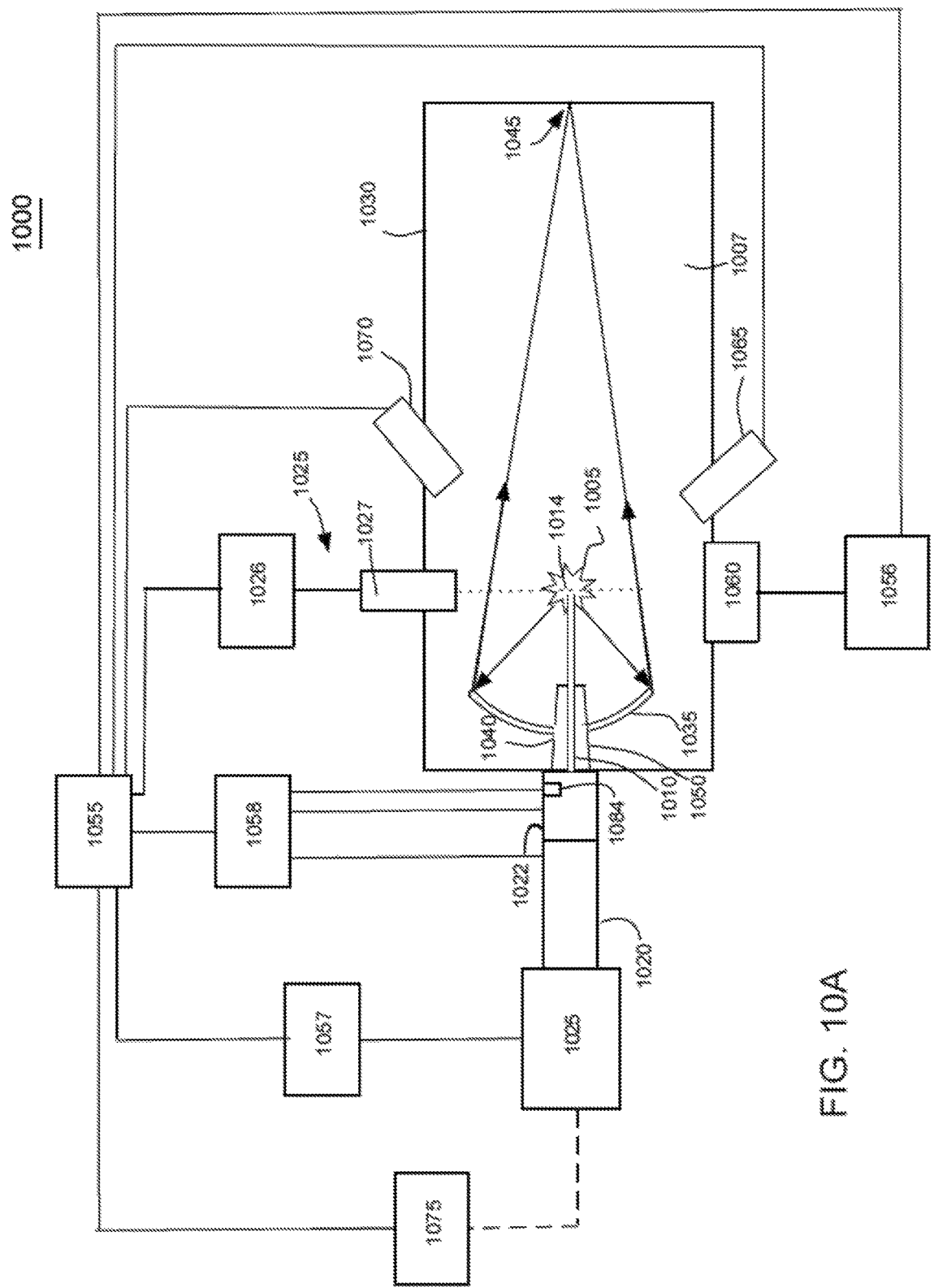
Figure 10B:
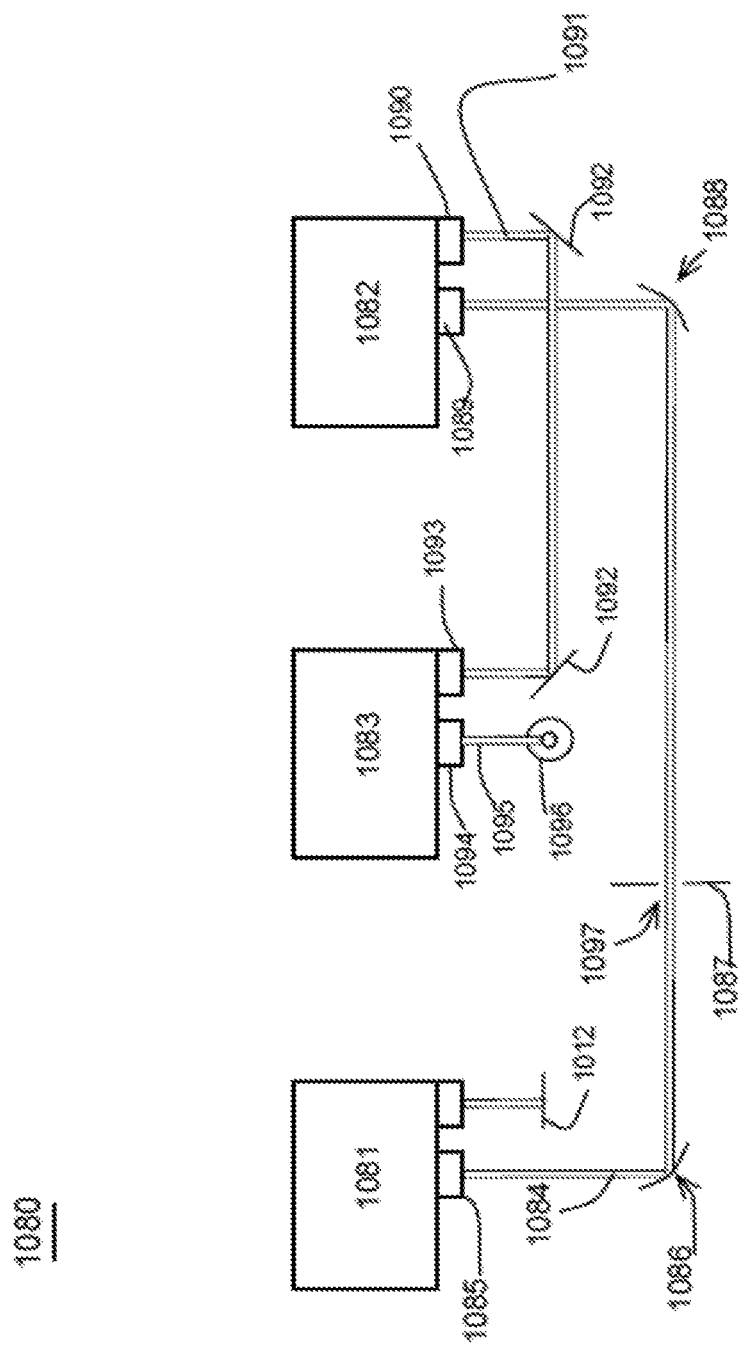

FIGS. 10A and 10B are block diagrams of an example of a EUV light source.

DETAILED DESCRIPTION

Figure 1:
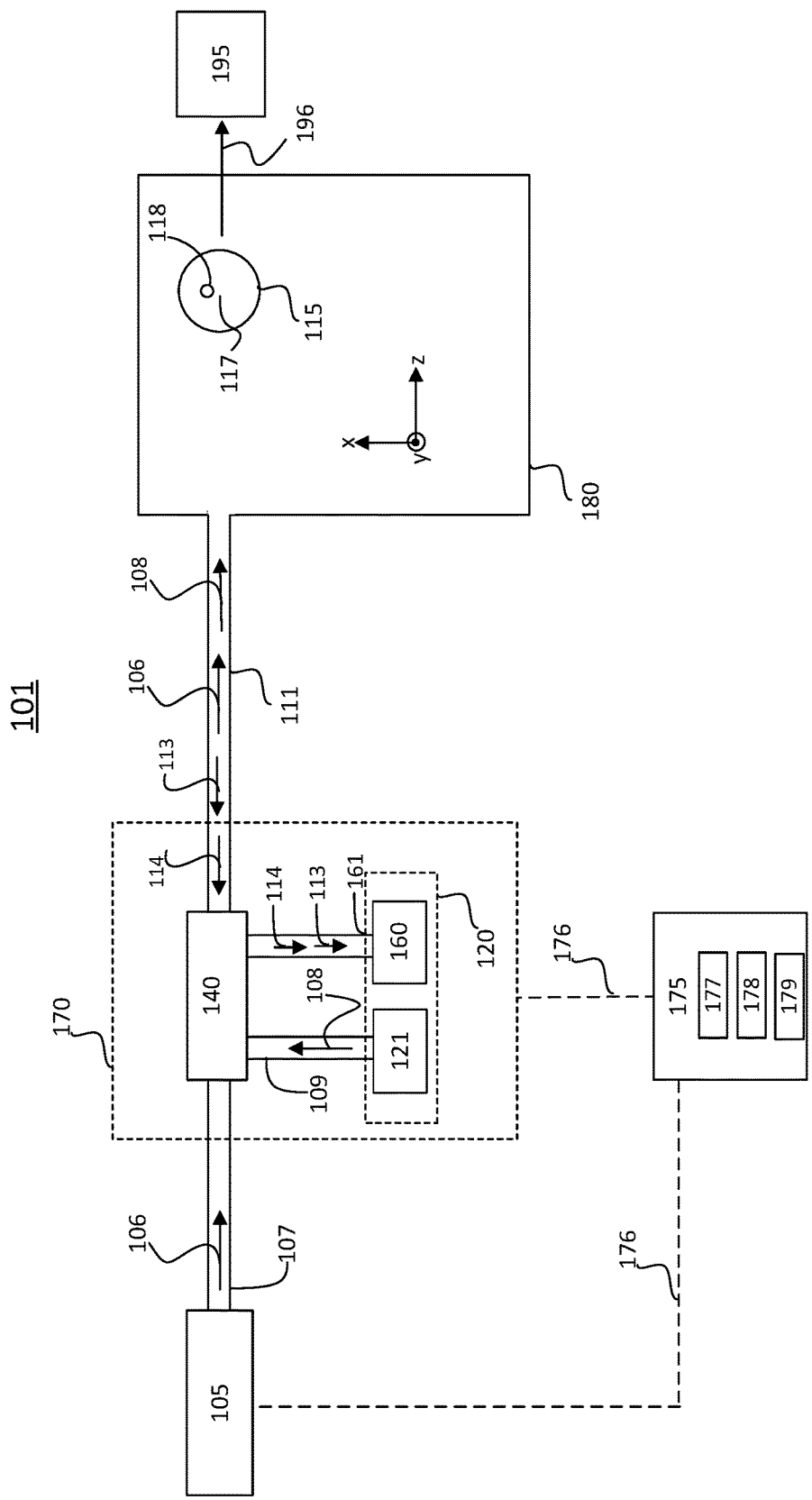
FIGS. 1 and 2 are block diagrams of examples of extreme ultraviolet (EUV) lithography systems.

Referring to FIG. 1, a block diagram of an example system 100 is shown. The system 100 includes an extreme ultraviolet (EUV) light source 101, which provides EUV light 196 to a lithography apparatus 195. The lithography apparatus 195 exposes a wafer (for example, a silicon wafer) with the EUV light 196 to form electronic features on the wafer. The EUV light 196 is emitted from a plasma that is formed by irradiating target material in a target 118. The target material is any material, such as, for example, tin, that emits EUV light in a plasma state. The plasma also may emit light having wavelengths other than the wavelengths of EUV light.

The EUV light source 101 includes a target metrology monitoring system 170 that monitors a target 118. The target metrology monitoring system 170 includes an optical beam combiner 140 and a metrology system 120. The optical beam combiner 140 allows a metrology light beam 108 to be inserted onto and/or directed along a path 111 toward a target region 115, which is in a vacuum vessel 180 and receives the target 118. The metrology light beam 108 is emitted by a metrology light source 121 onto a metrology path 109. The metrology light beam 108 interacts with the target 118 and produces a reflection 114 but does not change a property of the target material in the target 118 or convert the target material to EUV light. In other words, the metrology light beam 108 is an optical probe that generates the reflection 114 but does not disturb the target 118.

The target metrology monitoring system 170 directs the reflection 114 onto a detection path 161 toward a detection system 160. The detection system 160 includes one or more sensors and may include one or more optical elements configured to direct the reflection 114 toward the sensors. Examples of implementations of the detection system 160 are discussed in FIGS. 4A and 4B. The detection system 160 detects the reflection 114 and provides data representing the reflection 114 to a control system 175, which uses the data to monitor, estimate, and/or determine a property of the target 118. The property of the target 118 may be, for example, a position, velocity, or acceleration.

A light beam 106 is emitted by a light source 105 onto an initial path 107 toward the optical beam combiner 140. The optical beam combiner 140 directs the light beam 106 onto the path 111 and toward the target region 115 in the vacuum vessel 180. The light beam 106 and the metrology light beam 108 are pulsed light beams, and the beams 106 and 108 each include a train of pulses that are separated from each other in time. A pulse of the light beam 106 and a pulse of the metrology light beam 108 do not propagate through the optical beam combiner 140 at the same time. For example, the metrology light source 121 and/or the optical beam combiner 140 may be controlled such that a pulse of the metrology light beam 108 is emitted from the optical beam combiner 140 and onto the path 111 after one pulse of the light beam 106 but before the immediately subsequent pulse of the light beam 106.

An interaction between the target 118 and the light beam 106 modifies a property of the target (such as a geometric distribution of the target material in the target 118) and/or converts at least some of the target material into the plasma that emits the EUV light 196. Additionally, the interaction may generate a reflection. Light emitted by the plasma or the reflection may propagate on the path 111 in a direction different (for example, opposite) than the direction of the light beam 106. In FIG. 1, light emitted by the plasma and/or the reflection generated by the interaction of the light beam 106 and the target 118 is represented by the arrow labeled 113 and is referred to as the detection light 113.

In the example of FIG. 1, the target 118 travels in the -x direction (the coordinates shown in FIG. 1 are the coordinates of the vacuum vessel 180) toward an interaction location 117 in the target region 115. The interaction location 117 is a location where the target 118 is expected to coincide with the light beam 106 such that the light beam 106 and the target 118 interact sufficiently to modify a property of the target and/or convert at least some of the target material in the target 118 to plasma. Although the target 118 and the light beam 106 are expected to overlap at the interaction location 117, variations in the delivery of the target 118, the light beam 106, the initial path 107, and/or the path 111 may result in the target 118 and the light beam 106 not overlapping such that there is no interaction between the light beam 106 and the target 118 or an insufficient interaction between the light beam 106 and the target 118. For example, the target 118 may travel in the -x direction at a slower than expected speed. In this example, a pulse of the light beam 106 may pass through the interaction location 117 before the target 118, such that the target 118 and the pulse do not interact. In another example, the target 118 may drift in the x-y plane and away from the interaction location 117 such that the pulse and the target 118 do not interact. In another example, optical elements, such as mirrors and lenses, in the initial path 107 and/or the path 111 may experience thermal distortion or vibrations that may change the location of the light beam 106 in the vessel 180.

When the light beam 106 and the target 118 do not interact sufficiently to modify a property of the target 118 and/or convert target material to plasma, the performance of the EUV light source 101 may degrade. For example, the EUV light source 101 may produce less of the EUV light 196 as a result of missed interactions. As discussed below, the target metrology monitoring system 170 may reduce the occurrence of missed interactions or insufficient interactions.

Some legacy target tracking and monitoring systems rely exclusively or primarily on a reflection of the light beam 106 and/or non-EUV light emitted by the generated plasma to determine information (such as, for example, acceleration, position, and/or velocity) of the target 118, and the ability of such legacy systems to obtain information about the target 118 may be compromised when there is no interaction. However, in the target metrology monitoring system 170, the reflection 114 (which arises from an interaction between the target 118 and the metrology beam 108) is sensed or detected by the detection system 160 and provided to the control system 175 and used to monitor, determine, or estimate a property of the target 118. Thus, the target metrology monitoring system 170 does not rely exclusively on the detection light 113, and the target 118 may be monitored regardless of whether the light beam 106 interacts with the target 118 and regardless of whether the light beam 106 is generated. Additionally, by using the reflection 114, variations in the initial path 107 and/or the path 111 may be tracked independently of variations in the delivery of the target 118.

Although the target metrology monitoring system 170 does not rely on the detection light 113 exclusively, when the detection light 113 is present and enters the detection path 161, the detection system 160 uses both the detection light 113 and the reflection 114 to obtain addition information about the target 118.

Furthermore, the metrology light beam 108 is separate and independent from the light beam 106 and this also may lead to improved performance. For example, the metrology light beam 108 may be independent from the light beam 106 by being generated by a different light source and/or initially propagating on a different path than the light beam 106. Because the metrology light beam 108 and the light beam 106 are independent, the metrology light beam 108 may be modified to enhance the ability of the metrology light beam 108 to obtain information about the target 118 without also changing the properties of the light beam 106. For example, the metrology light beam 108 may be expanded such that a beam diameter of the metrology light beam 108 is at least as large as the largest diameter of the target region 115 (thereby increasing the probability of the metrology light beam 108 interacting with the target 118 and generating the reflection 114) without also having to enlarge a beam diameter of the light beam 106.

Additionally, the configuration of the target metrology monitoring system 170 allows the position of the target 118 to be determined in the coordinate system of the vessel 180. For example, because the metrology beam 108 and the light beam 106 follow the same path to the target region 115, the detection system 160 views the target 118 in the coordinates of the vessel 180. This may improve the accuracy of the position estimate by avoiding the need for the application of a position correction to the estimated or determined position of the target 118. In the example of FIG. 1, the metrology beam 108 and the light beam 106 propagate along the z direction in the vessel 180. Thus, the metrology beam 108 is orthogonal to the x and y directions in the vessel 180. Any or all of the sensors of the detection system 160 may be placed such that the horizontal and vertical axis of the sensor match the x and y coordinates of the vessel 180. As such, the detection system 160 produces data that represents the x and y directions in the vacuum vessel 180 without having to apply a correction factor.

The target metrology monitoring system 170 includes the control system 175, which communicates with the target metrology monitoring system 170 and the light source 105 via a communications path 176. The communications path 176 may be any type of wireless or wired connection capable of carrying control signals and information, and the communications path 176 may include more than one communications path. The control system 175 is able to control the emission of the light beam 106 based on the monitored property of the target 118. For example, the control system 175 may be configured to control the light source 105 to use a position of the target 118 estimated based on the reflection 114. For example, the control system 175 may use the estimated position of the target 118 to trigger the light source 105 to emit a pulse of the light beam 106 in a manner that ensures the light beam 106 and the target 118 are in the interaction location 117 at the same time.

The control system 175 includes an electronic processor 177, an electronic storage 178, and an input/output (I/O) interface 179. The electronic processor 177 includes one or more processors suitable for the execution of a computer program such as a general or special purpose microprocessor, and any one or more processors of any kind of digital computer. Generally, an electronic processor receives instructions and data from a read-only memory, a random access memory, or both. The electronic processor 177 may be any type of electronic processor.

The electronic storage 178 may be volatile memory, such as RAM, or non-volatile memory. In some implementations, and the electronic storage 178 includes non-volatile and volatile portions or components. The electronic storage 178 may store data and information that is used in the operation of the control system 175 and/or components of the control system 175.

The electronic storage 178 also may store instructions, perhaps as a computer program, that, when executed, cause the processor 177 to communicate with components in the control system 175, the optical beam combiner 140, the metrology system 120, and/or the light source 105. For example, the instructions may be instructions that cause the electronic processor 177 to generate a signal that results in the light source 105 emitting an optical pulse.

The I/O interface 179 is any kind of electronic interface that allows the control system 175 to receive and/or provide data and signals with an operator, the optical beam combiner 140, the metrology system 120, and/or the light source 105, and/or an automated process running on another electronic device. For example, the I/O interface 179 may include one or more of a visual display, a keyboard, and a communications interface.

Figure 2:
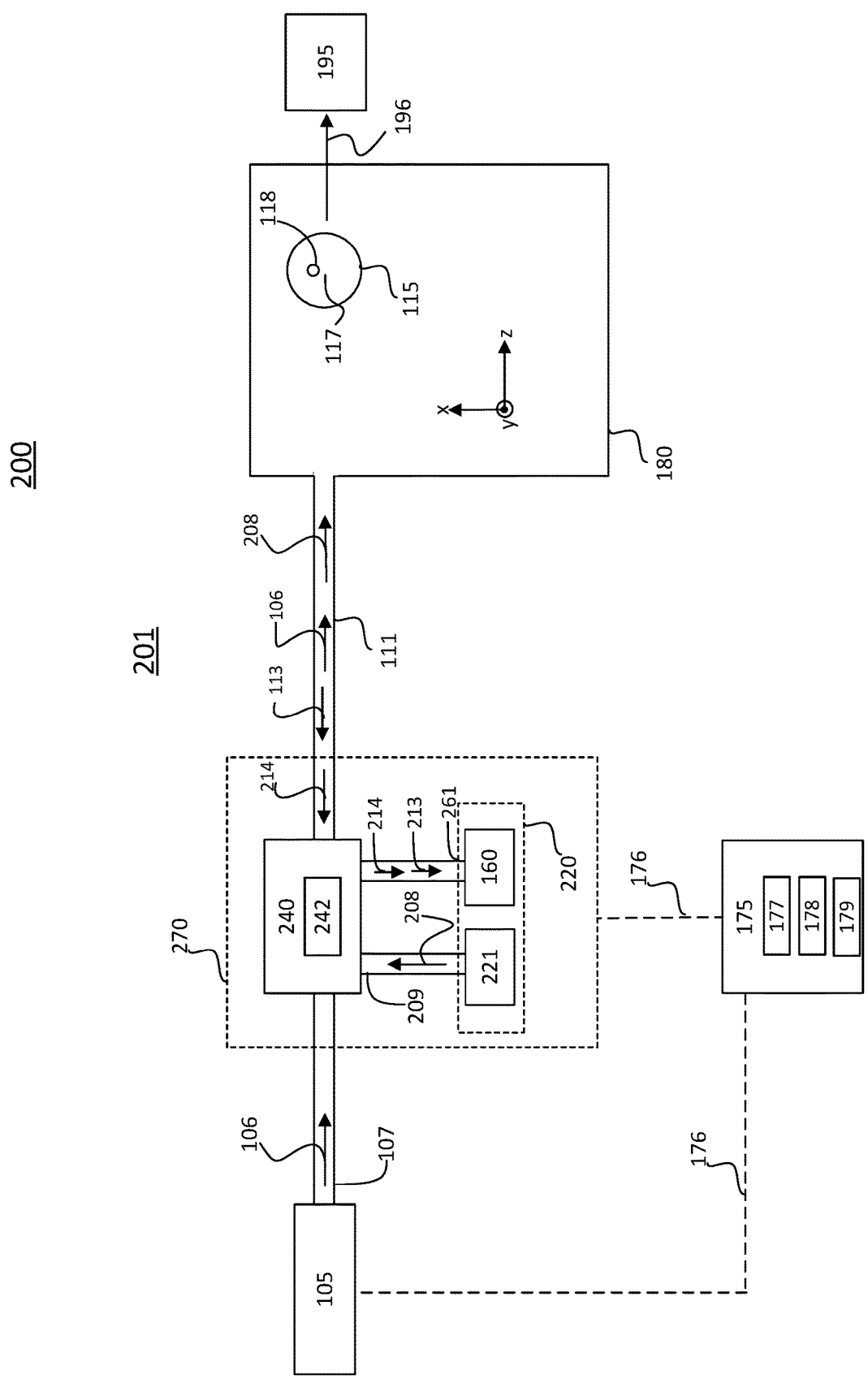

Referring to FIG. 2, a block diagram of another example of an EUV light source 201 is shown. The light source 201 includes a target metrology monitoring system 270, which may be used as the target metrology monitoring system 170 (FIG. 1). The target metrology monitoring system 270 includes a polarization-based optical beam combiner 240 that receives the light beam 106 and a metrology light beam 208, which is produced by a metrology light source 221. The polarization-based optical beam combiner 240 includes an optical modulator 242.

The polarization-based optical beam combiner 240 allows the light beam 106 and the metrology light beam 208 to be directed along the path 111 even if the metrology light beam 208 and the light beam 106 have the same spectral content. Additionally, the optical modulator 242 is controlled by the control system 175 such that the metrology light beam 208 and the light beam 106 have the same polarization state after passing through the optical modulator 242. The monitoring of the target 118 may be improved by the light beam 106 and the metrology light beam 208 having the same spectral content and the same polarization state. For example, by having the same spectral content, the beams 208 and 106 experience the same phase delay from passing through a wavelength-dependent optical element, such as a quarter-wave plate. This may lead to greater efficiency and improved metrology results.

The spectral content of a light beam may be the spectral power distribution, which represents the power per unit area per unit wavelength of the light beam. The metrology light beam 208 and the light beam 106 may have substantially the same spectral content by being produced by the same light source and separated into two beams, being produced by different instances of the same type of light source, being produced by different light sources that emit light of the same wavelength, or either or both of the beams 106 and 208 may be passed through a spectral filter such that the metrology light beam 208 and the light beam 106 have the same spectral content.

Regardless of the polarization states of the light beam 106 and the metrology light beam 208 when incident on the optical modulator 242, the light beam 106 and the metrology light beam 208 have the same polarization state after passing through the modulator 242. Polarization is a parameter that describes the direction of oscillation of the electric field of a light beam. A type of polarization and a direction of polarization define a polarization state. The type of polarization may be linear, circular, elliptical, or random, or the light beam may be unpolarized. A light beam that is linearly polarized has an electric field that oscillates in a single plane that is constant over time, with the polarization state indicating the plane of oscillation. For linearly polarized light, a polarization state in which the electric field oscillates in a first plane is orthogonal to a polarization state in which the electric field oscillates in a second plane that is orthogonal (for example, perpendicular) to the first plane. Linear polarized light that has an electric field polarized parallel to a plane of incidence may be referred to as P-polarized light, and S-polarized light is linearly polarized light that has an electric field perpendicular to the plane of incidence. Circularly polarized light has an electric field that describes a helix along the direction of propagation. Circularly polarized light may have different, orthogonal states. For example, circularly polarized light may be right-handed polarized light, in which the electric field rotates clockwise (as viewed from a point that receives the light), or left-hand polarized light, in which the electric field rotates counter-clockwise (as viewed from a point that receives the light).

FIG. 3A is a block diagram of an example EUV light source 301. The EUV light source includes a polarization-based optical beam combiner 340. The polarization-based optical beam combiner 340 is an example of an example implementation of the polarization-based optical beam combiner 240 (FIG. 2).

The EUV light source 301 may be used to generate the EUV light 196 for the lithography apparatus 195 (FIG. 1). The EUV light source 301 includes a target metrology monitoring system 370, which may be used as the target metrology monitoring system 170 in the EUV light source 101 (FIG. 1). The target metrology monitoring system 370 includes the polarization-based optical beam combiner 340, a metrology system 320, and a detection system 360. The polarization-based beam combiner 340 also includes an optical modulator 342. The polarization-based optical beam combiner 340 directs a light beam 306a, emitted from a light source 305a, and a metrology light beam 308, emitted from a metrology light source 325, toward a target region 315 on a beam path 311. In the example of FIG. 3A, only part of the beam path 311 is shown, but the beam path 311 is also present between A and A'. The light source 305a and the metrology light source 325 may be, for example, solid state lasers that emit light having a wavelength of 1.06 µm.

The light beam 306a and the metrology light beam 308 do not travel on the same portion of the beam path 311 at the same time. For example, the metrology light source 325 and the light source 305a may be pulsed light sources that are controlled by the control system 175 to emit pulses of light at different times. In another example, the light source 301 may include a mechanism (not shown) in the initial path 307 and the metrology beam path 309 that is controllable to block the beam 306a and/or 308, respectively, at certain times such that a pulse of the metrology light beam 308 and a pulse of the light beam 306a propagate through the optical modulator 342 at different times. The mechanism may include beam blockers or beam deflectors, for example.

The metrology light beam 308 interacts with a target 318 and generates a metrology reflection 314. The light beam 306a also may interact with the target 318 in the target region 315. Interactions between the target 318 and the light beam 306a may modify the geometric distribution of target material in the target 318 to form a modified target 319. The modified target 319 has a larger extent in the x-y plane than the target 318. The modified target 319 may be a disk shape. The interaction between the light beam 306a and the target 318 also may generate plasma and/or a reflection of the light beam 306a. The reflection and/or light emitted by the plasma (shown as detection light 313) may travel along the path 311 in a direction other than the direction in which the light beam 306a travels.

The modified target 319 moves generally in the −x direction toward a modified target region 316, where the modified target 319 interacts with a second light beam 306b that converts at least some of the target material in the modified target 319 to plasma that emits EUV light. In addition to emitting EUV light, the plasma also emits light having wavelengths in the detection band of the sensors in the detection system 360. A portion of the light emitted from the plasma (shown as detection light 312) may travel on the beam path 311 and into the target metrology monitoring system 370.

The metrology system 320 includes a metrology light source system 321. The metrology light source system 321 includes the light source 325 and a beam conditioning module 322. The beam conditioning module 322 includes one or more optical elements that act on the metrology light beam 308 to influence or modify the spatial profile of the metrology light beam 308 at the target region 315. For example, passing the metrology light beam 308 through the beam conditioning module 322 may cause the beam diameter of the metrology light beam 308 to increase such that, when the metrology light beam 308 reaches the target region 315, the beam diameter of the metrology light beam 308 is at least as large as than the greatest extent of the target region 315. The beam conditioning module 322 also may cause the metrology beam 308 to be collimated at the target region 315. The beam conditioning module 322 may include, for example, lenses, beam expanders, and linear polarizers.

The configuration of the metrology system 320 allows the spatial profile of the metrology light beam 308 to be modified without modifying the spatial profile of the light beams 306a and 306b. The metrology light beam 308 passes through the beam conditioning module 322 before reaching the polarization-based optical beam combiner 340. The light beams 306a, 305b do not pass through the beam conditioning module 322. Thus, the beam conditioning module 322 only modifies the spatial profile of the metrology light beam 308.

Because the target region 315 encompasses a volume of space through which the target 318 is expected to pass, increasing the beam diameter of the metrology light beam 308 increases the probability of generating the reflection 314. FIGS. 3B, 3C, and 3D illustrate, respectively, the target 318, the metrology light beam 308, and the light beam 306a in the x-y plane at the target region 315. The target 318 may be, for example, 30-40 µm in diameter. The diameter of the metrology light beam 308 with +/−7.5% uniformity may be large enough to encompass the field of view of the sensor 362. The field of view of the sensor 362 may be 320 µm×320 µm (shown as element 366 in FIG. 3C), and the diameter of the metrology light beam 308 with +/−7.5% uniformity may be 420 µm. The radius of the light beam 306a may be 100-200 µm. Other configurations may be used. For example, the field of view of the sensor 362 may be other than the example provided, and the diameter of the metrology beam may be expanded by a different amount.

Thus, the metrology light beam 308 is expanded to have a larger radius than the light beam 306a. The metrology light beam 308 may have a diameter that is, for example, 3-5 times greater or 30-50 times greater than the diameter of the light beam 306a and 10-15 times greater than the diameter of the target 318 at the target region 315. Additionally, the irradiance profile of the light beam 306a may be selected to be a top hat or Gaussian profile, for example.

Returning to FIG. 3A, the polarization-based optical beam combiner 340 includes two polarizing beam splitters (PBS) 343_1 and 343_2, the optical modulator 342, and a quarter-wave plate 344. A polarizing beamsplitter splits light by polarization state. For example, a PBS may transmit light of a first polarization state and reflect light of a second, orthogonal polarization state. The PBS 343_2 is closer to the target region 315 than the PBS 343_1. The optical modulator 342 is between the two polarization beam splitters 343_1 and 343_2, and the quarter-wave plate 344 is between the PBS 343_2 and the target region 315.

In the example discussed below, the PBS 343_1 and 343_2 transmit P-polarized light and reflect S-polarized light, the initial polarization state of the light beam 306a while the light beam propagates on the initial beam path 307 is P-polarized, and the initial polarization state of the metrology light beam 308 on the metrology path is S-polarized. Other configurations and polarization states are possible.

The light source 305a emits the light beam 306a onto the initial path 307 and toward the PBS 343_1. The light beam 306a reaches the PBS 343_1 and is transmitted toward the optical modulator 342. The light source 325 emits the metrology light beam 308. The metrology light beam 308 passes through the beam conditioning module 322, and is then incident on the PBS 343_1. The metrology light beam 308 is reflected toward the optical modulator 342 by the PBS 343_1.

After interacting with the PBS 343_1, the beams 306a and 308 are incident on the electro-optic modulator 342. An electro-optic modulator (EOM) is an optical device that includes an element (such as a crystal or a semiconductor) with an index of refraction that changes in response to the application of an electric field (for example, a voltage). Because the index of refraction of the element changes based on an applied voltage, a light beam passing through the element may be modulated by controlling the voltage applied to the element. For example, the polarization state of the light beam passing through the element of the EOM 342 may be modulated through the application of voltage.

The EOM 342 is controlled such that the light beam 306a and the metrology light beam 308 have the same polarization state after passing through the EOM 342. For example, the control system 175 may provide a signal to the target metrology monitoring system 370 indicating that a voltage be applied to the EOM 342 while the metrology light beam 308 is passing through the EOM 342. The voltage causes the index of refraction of the element in the EOM 342 to change, and the metrology light beam 308 becomes P-polarized by passing through the element of the EOM 342. Voltage is not applied to the EOM 342 while the light beam 306a passes through the EOM 342. Thus, the light beam 306a remains P-polarized.

Referring also to FIG. 3E, an example of a timing diagram 350 of voltage applied to the element of the EOM 342 as a function of time is shown. The process of applying and removing voltage illustrated in FIG. 3E may be continued throughout the operation of the light source 301 and the target metrology monitoring system 370. The timing diagram 350 includes five periods 351-355. Period 351 includes time (t=0) to time (t=t1). Voltage is not applied to the EOM 342 during the period 351, the EOM 342 does not affect the polarization state of incident light. Period 352 begins at time (t=t1) and ends at time (t=t2). During this time, voltage is applied to the element of the EOM 342. The rise time of the EOM 342 is a time that is equal to or less than t2−t1. Thus, by time (t=t2), the index of refraction of the element of the EOM 342 has been changed as necessary to modulate the polarization of an incident light beam. Period 353 begins at time (t=t2) and ends at time (t=t3). The voltage continues to be applied to the element of the EOM 342 during period 353. The metrology light beam 308 passes through the EOM 342 during the period 353, and the polarization state of the metrology light beam 308 is changed from S-polarization to P-polarization by passing through the element of the EOM 342. The voltage is removed from the element of the EOM 342 from time (t=t3) to time (t=t4), which is the period 354. The amount of time from time (t=t3) to time (t=t4) is equal to or greater than the rise time of the EOM 342. Thus, by the time (t=t4), the element of the EOM 342 has returned to the original index of refraction. The period 355 is from time (t=t4) to time (t=t5). During the period 355, no voltage is applied to the element of the EOM 342, and the beam 306a passes through the EOM 342 without changing polarization states.

The amount of time encompassed by each of the periods 351-355 depends on the characteristics of the EOM 342 and the operating parameters of the light source 301. For example, the rise time of the EOM 342 may determine the temporal spacing between a pulse of the light beam 306a and a pulse of the metrology beam 308. In some implementations, the rise time of the EOM 342 may be, for example, 3-10 microseconds (μs) and the period 353 (when the metrology light beam 308 passes through the EOM 342) may be 10-12 μs.

The light beam 306a and the metrology light beam 308 maintain the same polarization state as they propagate on the path 311. After passing through the EOM 342, the light beam 306a and the metrology light beam 308 are transmitted by the PBS 343_2 and pass through the quarter-wave plate 344. The quarter-wave plate 344 induces a 90° phase shift, changing the polarization state of the light beam 306a and the metrology light beam 308 to left-hand circularly polarized (LHCP). Because the light beam 306a and the metrology beam 308 have the same spectral content, the polarization-based elements, such as the quarter-wave plate 344, act on both beams in the same manner and the polarization states of the light beam 306a and the metrology light beam 308 remain the same after passing through the EOM 342.

Thus, the polarization-based optical beam combiner 340 injects the metrology light beam 308 onto the path 311 in a manner that causes the metrology light beam 308 and the light beam 306a to have the same polarization at the target region 315. The polarization-based optical beam combiner 340 also allows the metrology light beam 308 and the light beam 306a to be directed onto the beam path 311 while having the same spectral content. For example, the metrology light beam 308 and the light beam 306a may have a wavelength of about 1 micron (μm). In some implementations, the wavelength of the light beam 306a and the metrology light beam may be 1.06 μm.

After passing through the quarter-wave plate 344, the light beam 306a and the metrology light beam 308 continue to propagate on the beam path 311 and are directed toward the target region 315 by one or more optical components (represented by the optical component 304 in FIG. 3A). Although the beam 306a and the metrology light beam 308 propagate on the beam path 311, the beams may have some angular or lateral separation, and thus may be displaced laterally and are thus angularly separated along the x dimension at the target region 315. Pulses of the beams 308 and 306a arrive at the target region 315 at different times. In the example of FIG. 3A, the beam 308 arrives at the target region 315 before the first light beam 306a, and the location of the beam 308 in the target region 315 is displaced from the location of the beam 306a in the target region 315 in the x direction.

The metrology light beam 308 interacts with the target 318 and produces the reflection 314, which is right-hand circularly polarized (RHCP) in this example. The reflection 314 propagates back on the beam path 311 and through the quarter-wave plate 344. After passing through the quarter-wave plate 344, the reflection 314 has an S-polarization state. The reflection 314 is incident on the PBS 343_2, which reflects S-polarized light. Thus, the reflection 314 is reflected onto the detection path 361.

In the example of FIG. 3A, the light beam 306a interacts with the target 318 at the interaction location 317. The interaction between the light beam 306a and the target 318 produces the modified target 319 and also may produce a reflection of the light beam 306a (shown as the detection light 313). The detection light 313 propagates back along the path 311 as right-hand circularly polarized (RHCP), and is converted to S-polarized light by passing through the quarter-wave plate 344. The detection light 313 is thus also directed into the detection path 361. The metrology reflection 314 reaches the reflection path 361 before the detection light 313.

The metrology system 320 also includes the detection system 360, which includes sensors 362 and 365. The sensors 362 and 365 are positioned to receive portions of the reflection 314 and/or the detection light 313 from the detection path 361. In the example of FIG. 3A, beam divider 346 is positioned on the reflection path 361 between the PBS 343_2 and the sensor 365. The beam divider 346 may be any optical element capable of directing a portion of incident light toward the sensor 362 and a portion of the incident light toward the sensor 365. The beam dividers 364 may be, for example, a beam splitter.

The sensors 362 and 365 may be any type of sensor that is capable of sensing the wavelengths in the reflection 314 and the detection light 313. For example, the sensors 362 and 365 may include one or more of a camera, a photodiode, a position sensitive diode (PSD), a wavefront sensor, a spectrometer, or a quad cell. Additionally, either or both of the sensors 362 and 365 may be a system of sensors that includes more than one sensor. In some implementations (such as shown in FIG. 4A), each of various sensors in the detection system 360 may receive the reflection 314 and/or the detection light 313 in parallel.

In addition to the reflection 314 and the detection light 313, second detection light 312 also may propagate on the beam path 311 from the modified target region 316 toward the polarization-based optical beam combiner 340. The second detection light 312 includes light emitted from the plasma produced from an interaction between a light beam 306b and the modified target 319 and also may include a reflection of the light beam 306b. In the example of FIG. 3A, the light beam 306b travels along a path that is separate from the path 311 and is focused by a mirror 303 to a location in or near the modified target region 316. Although the light beam 306b does not travel on the path 311, it is possible for light emitted from the plasma that forms from an interaction between the light beam 306b and the modified target 319 to travel on the beam path 311. As discussed above, the plasma emits EUV light but also emits light of other wavelengths, including wavelengths in the detection band of the sensor 362. The detection light 312 thus also may enter the detection path 361 and may be detected by the sensors 362 and 365. The detection light 313 and the second detection light 312 pass through the quarter-wave plate 344. However, because the polarization state of the detection light 313 and the second detection light 312 is random, passing through the quarter-wave plate 344 does not affect or only negligibly affects the detection light 313 and the second detection light 312.

Referring to FIG. 4A, a block diagram of a detection system 460A is shown. The detection system 460A may be used as the detection system 160 (FIG. 1) or the detection system 360 (FIG. 3A). The detection system 460A includes a sensor 462, a sensor 463, and the sensor 365. In FIG. 4A, the arrows represent pulses of light that travel in the detection system 460A. The light that travels in the detection system 460A includes the reflection 314, and also may include the detection light 313 and/or the detection light 312.

The sensor 462 is an imaging sensor that captures two-dimensional information and is sensitive to the wavelengths in the reflection 314. Additionally, the sensor 462 is capable of being rapidly triggered between an ON state in which the sensor 462 detects light and an OFF state in which the sensor 462 does not detect light. For example, the sensor 462 may be capable of being triggered between the ON and OFF states at a rate of 50 kHz or greater. The sensor 462 is capable of capturing light over the entire time period during which the sensor is in the ON state. The sensor 462 may be, for example, a camera that includes a complementary metal oxide semiconductor (CMOS) sensor.

The sensor 463 may be any device capable of detecting light and producing a signal in response to detecting light. The sensor 463 may be a sensor that does not necessarily produce a two-dimensional representation of the detected light. For example, the sensor 463 may be a single photodiode or a photodector. An array of such devices may be used, and, in some implementations, the sensor 463 is capable of producing data that may be used to generate a two-dimensional representation of the detected light.

The detection system 460A also includes beam dividers 446_1 and 446_2, which divide incident light by reflecting some of the incident light and transmitting the remainder of the incident light. In the example of FIG. 4A, the beam dividers 446_1 and 446_2 are polarizing beam splitters (PBS) that reflect light of a first polarization state and transmit light of a second, orthogonal polarization state. The detection system 460A also includes half-wave plates 447_1 and 447_2. For linearly polarized light a half-wave plate (HWP) introduces a phase shift such that the linear polarization is rotated by twice the angle between the incident linearly polarized light and the half wave plates fast axis (that is, a HWP positioned at a 45 degree)(° tilt relative to incident linear polarization imparts a 90° rotation of the light that passes through the wave plate. The fast axis of the HWP may be oriented such that incident light having single linear polarization state emerges having components of two orthogonal linear polarization states.

In the example of FIG. 4A, the HWP 447_1 is between the PBS 343_2 and the beam divider 446_1, and the HWP 447_2 is between the beam divider 446_1 and the beam divider 446_2. Light having a first linear polarization state passes through the HWP 447_1 or the HWP 447_2 and emerges as light that has components that have the first linear polarization state and components that have a second linear polarization state that is orthogonal to the first.

The metrology reflection 314 is received at the PBS 343_2. As discussed above, the metrology reflection 314 may have an S-polarization state when incident on the PBS 343_2, and the PBS 343_2, which reflects light having an S-polarization state in this example, reflects the metrology reflection onto a detection path 461. The metrology reflection 314 passes through the HWP 447_1 and emerges with S-polarization and P-polarization components and is then incident on the beam divider 446_1. As discussed above, the beam dividers 446_1 and 446_2 are PBSs in this example. The beam divider 446_1 transmits the P-polarization portion of the reflection 314 toward the HWP 447_2 and reflects the S-polarization portion of the reflection 314 toward the sensor 462. The P-polarization portion of the reflection 314 passes through the HWP 447_2 and emerges with S-polarization and P-polarization components and is incident on the beam divider 446_2, which transmits the P-polarization portion toward the sensor 465 and reflects the S-polarization toward the sensor 463.

The detection light 313 and the detection light 312 follow paths through the detection system 460A that are similar to paths followed by the metrology reflection 314. However, because the detection light 313 and 312 are not exactly collinear with the metrology reflection 314, the reflection 314 and the detection light 313 and 312 may be incident on different regions of the sensor 462. Because the sensor 462 may be configured to collect light during the time when the reflection 314, the detection light 313, and the detection light 312 are incident on the sensor 462, all of the light reflected from the target region 315 and the modified target region 316 may be represented on a single image. An example of a visual representation that may be produced using data from the sensor 462 and the sensor 463 is discussed with respect to FIGS. 8A, 8B, and 9A-9C.

Referring to FIG. 4B, a block diagram of another detection system 460B is shown. The detection system 460B may be used as the detection system 360 (FIG. 3A) or the detection system 160 (FIG. 1). The detection system 460B is similar to the detection system 460A, except the detection system 460B includes a polarization-based optical isolation system 443 between the PBS 343_2 and the beam divider 446_1. The polarization-based optical isolation system 443 is used to prevent either the reflection 314 or the detection light 313 from entering the detection path 461. The arrows shown in FIG. 4B represent a pulse of light that passes through the polarization-based optical isolation system 443 and onto the detection path 461.

The polarization-based optical isolation system 443 includes an electro-optic modulator 442 and a PBS 447. The second electro-optic modulator 442 is controlled by the control system 175 (FIG. 1, FIG. 2, and FIG. 3A) to adjust the polarization state of light that passes through a crystal element of the electro-optic modulator 442. The electro-optic modulator 442 may be the same as the electro-optic modulator 342 (FIG. 3A).

The electro-optic modulator 442 may be controlled to change the polarization state of one of the reflection 314 and the detection light 313 (whichever is intended to not enter the detection path 361) to an orthogonal polarization state. The control system 175 controls the electro-optic modulator 442 by causing a voltage to be applied to the element of the modulator while the light that is intended to be removed from the detection path 461 passes through the element, causing the polarization state of the light to change. When the other light beam passes through the electro-optic modulator 442, the voltage is not applied and the polarization state of the light does not change.

After passing through the optical modulator 442, the reflection 314 and the detection light 313 interact with the PBS 447. The PBS 447 is oriented to transmit light of a first polarization state onto the detection path 461 and to reflect light of a second, orthogonal polarization state away from the detection path 461. Thus, light having the second polarization state does not enter the detection path 461. The electro-optic modulator 442 is controlled to change the polarization of one of the reflection 314 and the detection light 313 such that only one of these beams enters the detection path 461 and is detected by the sensors 462, 463, and 365.

Referring to FIG. 5, a block diagram of an EUV light source 501 is shown. The EUV light source 501 includes a target metrology monitoring system 570. The target metrology monitoring system 570 includes a metrology system 521 and the detection system 460A (FIG. 4A). The target metrology monitoring system 570 also may be used with the detection system 460B (FIG. 4B).

The target metrology monitoring system 570 differs from the target metrology monitoring system 370 (FIG. 3A) in that the target metrology monitoring system 570 does not include an electro-optic modulator. Instead, the target metrology monitoring system 570 includes a wavelength-based optical beam combiner 540. The wavelength-based optical beam combiner 540 includes a dichroic optical element 548 that transmits or reflects light based on the spectral content of the light.

The metrology system 521 includes a metrology light source 525 that emits a metrology light beam 508. The metrology light beam 508 and the first light beam 306a do not include the same spectral content. For example, the metrology light beam 508 may include one or more wavelengths that are different than the wavelength or wavelengths of the first light beam 306. In some implementations, the first light beam 306a may be produced by a CO2 laser and includes light having a wavelength of 10.6 µm, and the metrology light beam may include light having a wavelength of, for example, 532 nm to 1550 nm (for example, 1550 nm, 1064 nm, 980 nm, 908 nm, 820 nm, 808 nm, or 532 nm) However, like the target metrology monitoring system 370 (FIG. 3A), the target metrology monitoring system 570 directs the metrology light beam 508 and the first light beam 306a toward the target region 315 with the same polarization state.

The metrology light source 525 emits the metrology light beam 508 onto a metrology light beam path 509. The metrology light beam 308 has an initial polarization state. The metrology light beam 508 may pass through a beam conditioning module 522, which expands (and also may collimate) the metrology light beam 508 in the x-y plane at the target region 315. The beam conditioner 522 may be similar to the beam conditioner 322 (FIG. 3A). In the example of FIG. 5, the beam conditioner 522 may include one or more passive polarizing elements (such as a half wave plate) that modifies the polarization state of the metrology light beam 508 before reaching a PBS 543 such that the metrology light beam 508 is reflected by the PBS 543. In this example, the metrology light beam 508 is reflected from the PBS 543 in a linearly polarized state and passes through a quarter-wave plate 544_1, which converts the metrology light beam 508 to a circularly polarized light state.

The metrology light beam 508 is then directed (for example, by a mirror 504) toward the dichroic optical element 548. The dichroic optical element 548 may be any optical element capable of transmitting and reflecting light based on the wavelength of the light. For example, the dichroic optical element 548 may be a partially reflective mirror that transmits light having wavelengths in a first band of wavelengths and reflects light having wavelengths in a second band of wavelengths. The dichroic optical element 548 may be a dichroic beam splitter. The metrology light beam is incident on the dichroic optical element 548 and is directed onto a beam path 511 toward the target region 315. In the example of FIG. 5, the metrology light beam 508 is directed onto the beam path 511 by being transmitted through the dichroic optical element 548. In FIG. 5, only part of the beam path 511 is shown, but the beam path 511 is also present between A and A'.

The first light source 305a emits the first light beam 306a onto an initial beam path 507. While on the initial beam path 507, the first light beam 306a has a linear polarization state (for example, P-polarized or S-polarized). The first light beam 306a passes through a quarter waveplate 544_2 and becomes circularly polarized (for example, RHCP or LHCP). The first light beam 306a is directed toward the dichroic optical element 548 and directed onto the beam path 511. As discussed above, the first light beam 306a and the metrology light beam 508 do not have the same spectral content. The metrology light beam 508 is transmitted through the dichroic optical element 548. However, the first light beam 306a is reflected by the dichroic optical element 548 and is thus also directed onto the beam path 511.

Any combination of passive polarizing optical elements may be used in the metrology light beam path 509 and the initial beam path 507 such that the metrology light beam 508 and the first light beam 306a have the same polarization state when incident on the dichroic optical element 548. The dichroic optical element 548 does not change the polarization state of the metrology light beam 508 or the first light beam 306a. Thus, due to polarizing optical elements such as the quarter wave plates 544_1 and 544_2, both the first light beam 306a and the metrology light beam 508 have the same polarization state after interacting with the dichroic optical element 548.

The metrology light beam 508 interacts with the target 318 and produces a metrology reflection 514 that travels on the beam path 511. While on the beam path 511, the metrology reflection 514 has a circular polarization state that is orthogonal to the circular polarization state of the metrology light beam 508. The metrology reflection 514 is transmitted by the dichroic optical element 548 and is incident on the quarter wave plate 544_1. The metrology reflection 514 emerges from the quarter wave plate 544_1 with a linear polarization state that is orthogonal to the polarization state of the metrology light beam 508 before passing through the quarter wave plate 544_1. Thus, the metrology reflection 514 is transmitted by the PBS 543 and enters the detection system 460A. Detection light 313 and 312 having the same spectral content as the reflection 314 also may enter the detection path 361. The detection path 361 is part of the detection system 460A and is shown in FIG. 4A.

Referring to FIG. 6, a flow chart of an example of a process that may be used to determine a property of a target is shown. The process 600 may be performed with any EUV light source. For example, the process 600 may be performed by any of the EUV light sources 101, 201, 301, or 501. The various features of the process 600 may be performed by the electronic processor 177 of the control system 175. Although the process 600 may be performed with any of the EUV light sources discussed above, for the purpose of providing an example, the process 600 is discussed with respect to the EUV light sources 301 (FIG. 3A) and 501 (FIG. 5).

The metrology light beam 308 is directed toward the target region 315 onto the beam path 311 (610). The metrology light beam 308 has a wavelength or wavelengths, which may be described by a spectral content. The metrology light beam 308 also has a polarization state. For example, the metrology light beam 308 may be left-hand circularly polarized light. In the example of FIG. 3A, the metrology light beam 308 is directed onto the beam path 311 by the polarization-based optical beam combiner 340. However, a metrology light beam may be directed onto a beam path in other ways. For example, as shown in FIG. 5, the metrology light beam 508 is directed onto a beam path 511 with the dichroic optical element 548.

The first light beam 306a is directed onto the beam path 311 toward the initial target region 315 (620). Thus, both the metrology light beam 308 and the first light beam 306a travel on the beam path 311 toward the initial target region 315.

The first light beam 306a and the metrology light beam 308 have the same polarization state on the beam path 311. The first light beam 306a and the metrology light beam 308 pass through the optical modulator 342. The optical modulator 342 is controlled such that a voltage is applied at an appropriate time to ensure that the first light beam 306a and the metrology light beam 308 have the same polarization state after passing through the modulator 342. For example, if the first light beam 306a and the metrology light beam 308 initially have different polarization states, then the control system 175 may apply a voltage to the modulator 342 when the metrology light beam 308 passes through the modulator 342 but not when the first light beam 306a passes through the modulator 342 (or vice versa).

In some implementations, such as the EUV light source 501 (FIG. 5), an electro-optic modulator is not used. Instead, passive polarization elements, such as half wave plates, linear polarizers, and/or quarter wave plates are used to control the polarization state of the metrology light beam 508 and the first light beam 306a in their respective paths 509 and 507. In these implementations, the first light beam 306a and the metrology light beam 508 do not have the same spectral content.

In some implementations, the first light beam 306a is directed toward the target region 315 based on receiving a reflection of a metrology light beam, such as the metrology reflection 314 (FIG. 3A) or the metrology reflection 514 (FIG. 5). In these implementations, the control system 175 may be configured to trigger the light source 305a to produce the first light beam 306a only after the reflection 314 is detected. Configuring the control system 175 in this manner may improve the performance of the light source 301 or 501. For example, if the light source 305a is triggered to always produce the first light beam 306a or to produce the first light beam 306a at a pre-determined regular interval, the first light beam 306a may arrive in the target region 315 without overlapping with the target 318. By triggering the first light source 305a to produce the first light beam 306a only after the metrology reflection 314 is received, the probability of an interaction between the first light beam 306a and the target 318 is increased.

Additionally, directing the first light beam 306a toward the target region 315 based on a reflection of a metrology light beam also allows the position of the target 318 to be estimated close to the time when the first light beam 306a is expected to be in the target region 315, which may provide a further performance improvement. For example, the control system 175 may receive a representation of the detected metrology reflection 514, such as, for example, data sufficient to form a two-dimensional image of the target region 315 with the metrology reflection 314. The processor 177 may execute instructions stored on the electronic storage 178 to estimate a position of the target 318 in the target region 315 based on the representation of the detected metrology reflection 514. For example, the control system 175 may analyze the representation to determine the location of the center of mass of the target 318 in an image produced by the sensor 362 and may estimate the position of the target 318 in the x-y plate at the target region 315 based on the center of mass. In another example, the control system 175 may apply a morphological operator to the representation to detect the edges of the target 318 in the representation of the reflection 314 and may estimate the position of the target 318 in the x-y plane at the target region 315 based on the detected edges.

The control system 175 may provide the estimated position to the light source 305a such that the light source 305a emits the light beam 306a at a time when it is likely to result in the light beam 306a and the target 318 overlapping. Additionally or alternatively, the control system 175 may provide a signal to controllable optical components (such as mirrors and lenses) between the light source 305a and the target region 315 to adjust the pointing and/or focal point of the light beam 306a.

The second light beam 306b is directed toward the modified target region 316 (630). In the EUV light sources 301 and 501, the second light beam 306b travels on a separate path than the path 311. The second light beam 306b interacts with the modified target 319 and converts at least some of the target material in the modified target 319 into plasma that emits EUV light.

The plasma also emits light at wavelengths other than the wavelengths of the EUV light, including detection light 312, which includes light at wavelengths in the detection band of the sensors of the detection system 460A. The detection light 312 may travel on the light path 311 as shown in FIG. 3A.

Referring to FIG. 7, a flow chart of an example of a process 700 that generates a representation of a region inside of a vacuum vessel of an EUV light source is shown. The region inside the vacuum vessel includes the target region 315 and the modified target region 316 shown in FIG. 3A. The process 700 may be performed by the electronic processor 177 of the control system 175. The process 700 is discussed with respect to the EUV light source 301 (FIG. 3A) and the detection system 460A (FIG. 4A). However the process 700 also may be used with the EUV light sources 101, 201, and 501.

Light associated with the metrology light beam 308 is received from the target region 315 (710). For example, the metrology reflection 314 may be received at the sensor 462 (FIG. 4A). The sensor 462 is a sensor that is capable of sensing light in a two-dimensional region. Thus, data produced by the sensor 462 is capable of providing two-dimensional spatial information about light detected by the sensor 462. For example, the sensor 462 may provide information that indicates where on the sensor 462 light is detected. Additionally, the sensor 462 is capable of sensing light over time (for example, during an exposure period).

Light associated with the first light beam 306a is received from the target region 315 (720). For example, the detection light 313 may be received at the sensor 462 (FIG. 4A). The detection light 313 is received at the sensor 462 after the metrology reflection 314 is received. As discussed above, the detection light 313 and the metrology reflection 314 are received at different portions of the sensor 462.

A representation of the metrology light beam 308 and the first light beam 306a is generated based on the received light associated with the metrology light beam 308 and the received light associated with the first light beam 306a (730). The representation includes two-dimensional spatial information related to the metrology light beam 308 and the first light beam 306a in the target region 315. Additionally, in some implementations, light associated with the second light beam 306b is also received at the sensor 462. For example, the detection light 313 may be received at the sensor 462, and the generated representation may include two-dimensional spatial information about the light beam 306b in the target region 315.

Figure 8A:
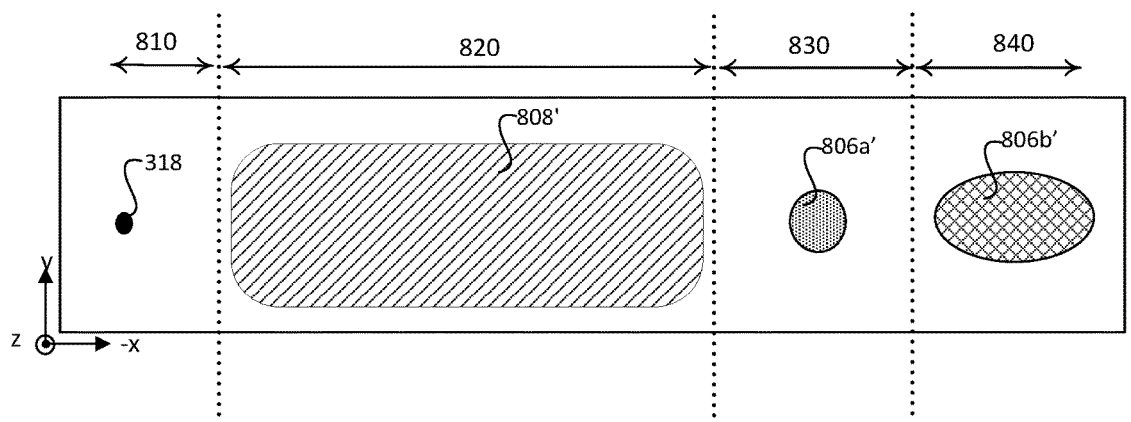

Referring to FIG. 8A, an example of a two-dimensional plot 800A generated by the process 700 is shown. The plot 800A is in an x-y plane of a region inside a vacuum vessel (such as the vessel 180 of FIG. 1) that includes the target region 315 and the modified target region 316. The plot 800A shows the progression of the target 318 in the −x direction through the target region 315 and the modified target region 316. The −x direction is the direction opposite to the x direction shown in FIGS. 1, 2, 3A, and 5. The plot 800A is formed from a reflection 314 that arises from a pulse of the metrology light beam 308 interacting with the target 318.

The plot 800A includes four spatial regions 810, 820, 830, and 840 that correspond to four regions in the vacuum vessel. The target 318 traverses the region 810 first, followed by the regions 820, 830, and 840 in order. In the region 810, none of the metrology light beam 308, the first light beam 306a, and the second light beam 306b interact with the target 318. The region 810 is displaced in the x direction relative to the target region 315. In other words, the target 318 passes through the region 810 before reaching the target region 315. The beginning of the region 810 may correspond to the initial detection of the target 318 or the moment when the target 318 enters the vacuum vessel 180. In some implementations, the sensor 462 may start collecting data (and the region 810 may begin) when the target 318 passes through a light curtain that is separate from the metrology light beam 308. The light curtain may be a continuous wave laser or other light beam that is oriented to emit light in the vacuum vessel 180 (FIG. 1) along the z direction and perpendicular to the direction of motion of the target 318. The light curtain is displaced in the x direction relative to the target region 315 or the target region 115 (FIG. 1) such that the target passes through the light curtain prior to interacting with the metrology light beam 308 and the light beam 306a.

The target 318 interacts with a pulse of the metrology light beam 308, and the reflection 314 is detected at the sensor 462. The sensor 462 detects the reflection 314 for as long as the reflection is produced and a representation 808' of the metrology light beam 308 is formed. The size of the representation 808' provides an indication of where the metrology light beam 308 and the target 318 interact. When the target 318 interacts with a pulse of the light beam 306a, the sensor 462 detects the detection light 313. A representation 806a' of the first light beam 306a in the target region 315 is formed in the region 830 of the plot 800A. The sensor 462 detects the detection light 312 and a representation 806b' of the second light beam 306b is formed in the region 840 of the plot 800A.

Additionally, the times at which the metrology light beam 308 and the first light beam 306a interact with the target 318 and the time at which the second light beam 306b interacts with the modified target 319 may be determined from the sensor 463 (FIG. 4A). The reflection 314 and the detection light 313, 312 is also received at the sensor 463. As discussed above, the sensor 463 is a photo-diode. The photo-diode provides an indication of when light is initially received to the control system 175. Thus, information from the photo-diode may be used to determine when the reflection 314 and the detection light 313, 312 is received at the sensor 462.

The spatial coordinates of the plot 800A correspond to the spatial coordinates in an x-y plane in the vacuum vessel that includes the target region 315 and the modified target region 316. In the example of FIG. 8A, the region 810 has an extent along the x direction of about 300 µm, the region 820 has an extent along the x direction of about 560 µm, the region 830 has an extent along the x direction of about 266 µm. The x-direction may be a direction that is parallel to the direction in which the target 318 travels in the target region 315.

In the example of FIG. 8A, the representations 808', 806a', and 806b' are shown with visually distinct display styles (slanted lines, dots, and cross-hatching, respectively) so that each representation is easily distinguished by an operator of the EUV light source 301. Other visually distinct display styles, such as different colors, may be used to distinguish the various representations to a human operator and/or an automated process that executes at, for example, the processor 177 of the control system 175.

Additionally, the two-dimensional plot 800A may be used to determine one or more properties of the target 318. For example, the centroid of the representation 806b' may be determined to estimate a location of the interaction site 317 in the target region 315. In another example, a location of the initial interaction between the metrology light beam 308 and the target 318 may be estimated from the representation 808', and a location of the interaction site 317 may be estimated from the representation 806b'. This data provides two estimated locations of the target 318 in the target region 315. Additionally, because the time difference is know from the sensor 362, the velocity of the target 318 may be estimated.

Thus, the two-dimensional plot 800A provides a visualization tool for an operator of the EUV light source 301 and also may be used to estimate properties of the target 318.

Figure 8B:
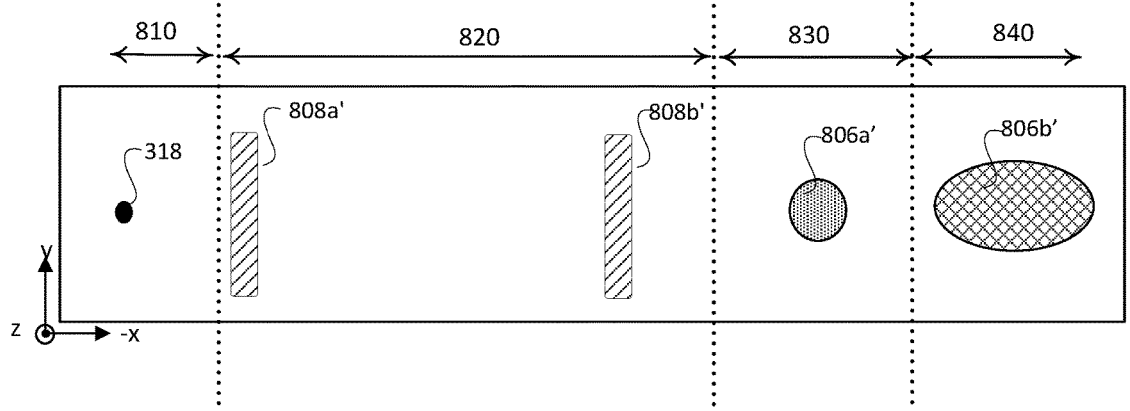

FIG. 8B shows a plot 800B. The plot 800B is another example of a plot that may be generated from the process 700. The plot 800B is similar to the plot 800A except, in the plot 800A, the light associated with a metrology light beam received from an interior of the vacuum vessel that includes the target region 315 and the modified target region 316 arises from the interaction of two continuous-wave (that is, non-pulsed) light beams. Thus, two separate reflections from two separate metrology light beams are received at the sensor 462. The two separate metrology light beams may be different than and separate from the metrology light beam 308. For example, the two separate metrology light beams may be light curtains that are continuously generated and propagate in the z direction within the vacuum vessel 180 (FIG. 1) at a location that is displaced in the x direction relative to the interaction location 317. Like the metrology light beam 208, the light curtains do not change a property of the target 318 and the interaction between the light curtains and the target 318 only generates reflections that may be detected at the sensor 362. The detected reflections are presented as representations 808a' and 808b' in the plot 800B. As such, the light associated with a metrology light beam that arrives in the detection system 360 may arise from a metrology light beam other than the metrology light beams 108, 208, 308, and 508 discussed above.

Figure 9A:
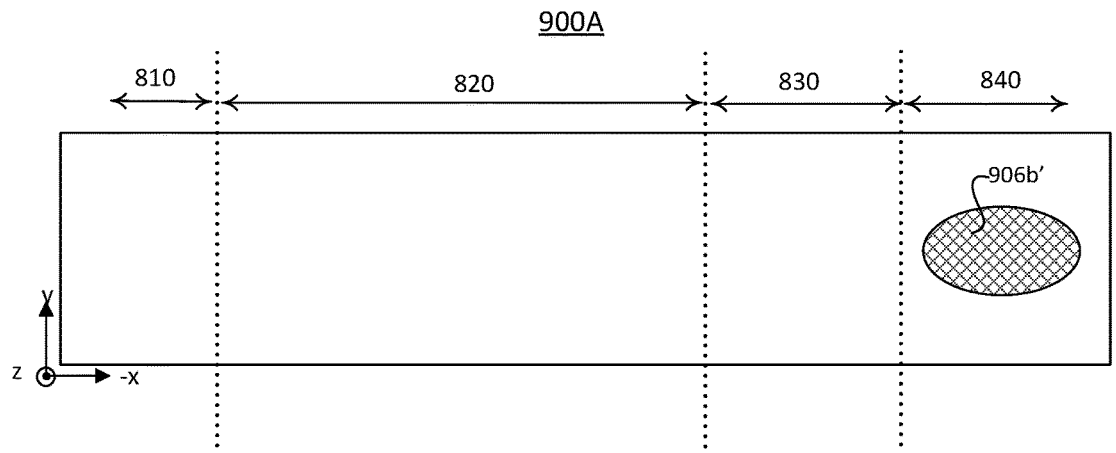
Figure 9B:
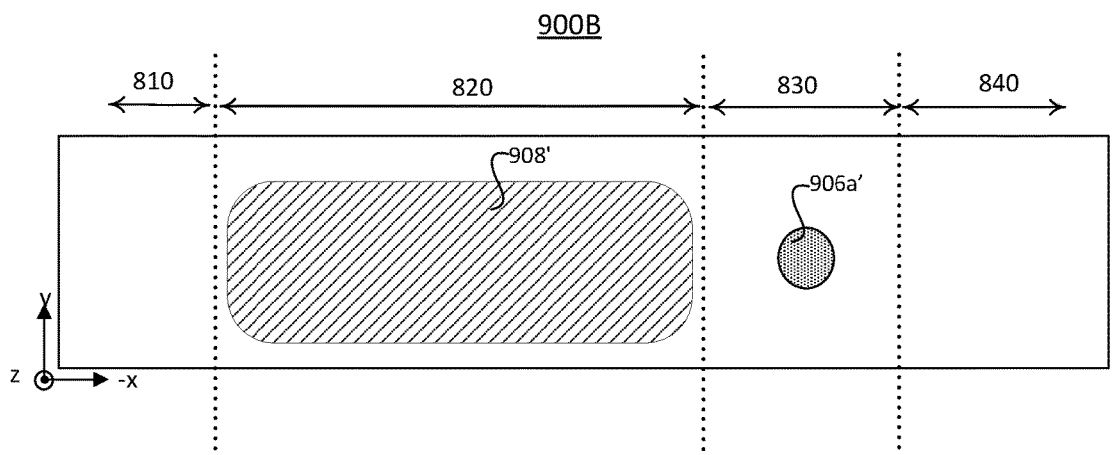
Figure 9C:
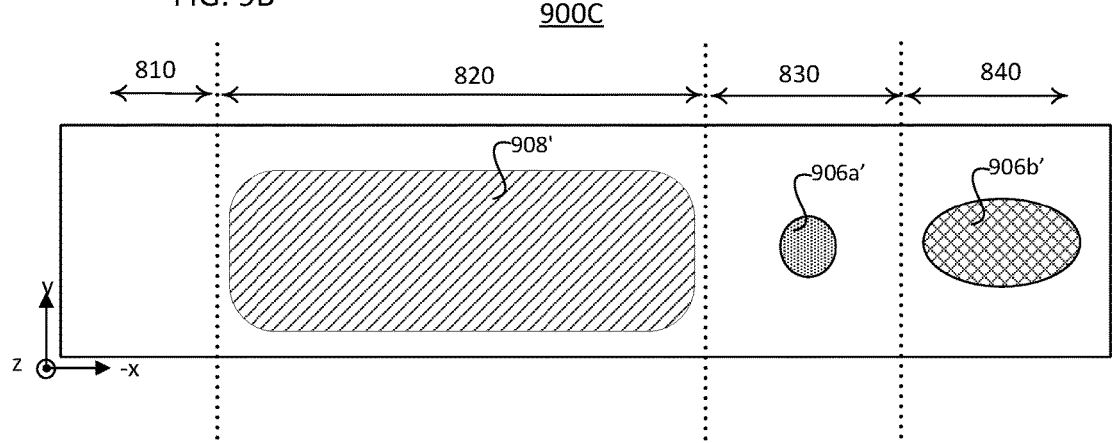

Referring to FIG. 9C, an additional example of a plot 900C is shown. The plot 900C is a two-dimensional plot similar to the plot 800A (FIG. 8A). However, the plot 900C is formed by combining or fusing data from two separate plots 900A (FIG. 9A) and 900B (FIG. 9B).

FIGS. 9A-9C also illustrate an example of plasma filtering. Plasma filtering is a timing technique used to control the sensor 462 such that an interaction between the light beam 306b and the modified target 319 is not captured in each frame of data produced by the sensor 462.

The plasma filtering is possible because of the ability of the sensor 462 to trigger between an ON and an OFF state rapidly. For example, the sensor is able to trigger between the ON and the OFF states at 50 kHz or greater, allowing the sensor 462 to be ON when a pulse of the light beam 306a and the modified target 319 interact to form plasma and OFF for the immediately subsequent modified target. This triggering allows an image of reflection 314 and the detection light 313 to be obtained without the detection light 312 also being obtained in the same frame. The detection light 312 is typically much brighter than the reflection 314 and the detection light 313. Thus, preventing the imaging of the detection light 312 or reducing the amount of detection light 312 may produce improved representations of the metrology light beam 308 and the first light beam 306a. The sensor 462 may be transitioned to the ON state by opening a shutter that allows light to reach the sensor 462 and may be transitioned by closing the shutter and preventing light from reaching the sensor 463.

The plot 900A (FIG. 9A) is obtained from a first frame of data. To generate the plot 900A, the sensor 462 is in the OFF state while the reflection 314 and the detection light 313 propagate in the detection system 460A. The sensor 463 is ON and detects the presence or absence of the reflection 314 and the detection light 313. After the sensor 463 detects the detection light 313 and the absence of the detection light 313 (indicating that the interaction between the light beam 306a and the target 318 has ended) but before the detection light 312 is detected by the sensor 363, the control system 175 triggers the sensor 462 ON. The sensor 462 detects the detection light 312 and provides the data to the control system 175. The control system 175 forms the plot 900A from the data provided by the sensor 462. The plot 900A includes a representation 906b', which is a representation of the detection light 312.

The plot 900B (FIG. 9B) is obtained from a second frame of data from the sensor 462. The second frame of data is separate from the first frame. As shown in FIG. 3A, the target 318 is one of many targets that enter the target region 315 over time. The target 318 is target n, and the immediately subsequent target is referred to as target (n+1). The target n+1 is labeled on FIG. 3A. The sensor 462 is triggered ON by the detection of the target n+1. The target n+1 may be detected by a light curtain that is separate from the metrology light beam 308 or the target n+1 may be detected by the release of a target from a target supply, for example.

After the sensor 462 is triggered ON a reflection from the target n+1 (similar to the reflection 314) and detection light from the interaction between another pulse of the light beam 306a and the target n+1 (similar to the detection light 313) are sensed by the sensor 462. After the detection light from the interaction between the target n+1 and the light beam 306a ends and before another pulse of the light beam 306b interacts with the modified target n+1, the sensor 462 is triggered OFF. Thus, the sensor 462 does not detect light emitted from the second plasma event in the second frame of data.

The sensor 462 provides the data of the second frame to the control system 175, which forms the plot 900B from the data. The plot 900B includes the representations 908' and 906a'. The representation 908' is a representation of another pulse of the metrology light beam 308 interacting with the target n+1. The representation 906a' is a representation of another pulse of the light beam 306a interacting with the target n+1. The plot 900B does not include a representation of light emitted by a plasma formed when another pulse of the light beam 306b interacted with a modified target.

The plot 900C is formed by combining, spatially overlaying, superimposing (through a matrix sum), or fusing the plots 900A and 900B. For example, the plot 900A is stored in the electronic storage 178, and the plot 900B is then captured and stored in the electronic storage 178. The plots 900A and 900B are stored as images with an integer associated with each pixel. Because the plots 900A and 900B are from the same sensor, the plots 900A and 900B have the same number of rows and columns. Thus, the plots 900A and 900B may be combined to form the plot 900C by adding the data that represents the plot 900A to the data that represents the plot 900B. In this example, the addition is the superposition of the two images, which may be achieved mathematically by a matrix sum of two scalar (monochrome) images.

Additionally, the sensor 462 may be a camera with the exposure open as the target 318 travels through the regions 810-840. The camera integrates (adds) the signals, and, if spatial resolved, the relative spatial location of the signal is apparent. In this example, the sensor 463 is a photodiode that provides temporal information (the time of each detected signal). The spatial information from the camera 462 and the temporal information from the photodiode 462 may be used to reconstruct the path of the target 318.

Referring to FIG. 10A, an LPP EUV light source 1000 is shown. The target metrology monitoring systems 170, 270, 370, and 570 may be part of an EUV light source, such as the source 1000. The LPP EUV light source 1000 is formed by irradiating a target mixture 1014 at a target region 1005 with an amplified light beam 1010 that travels along a beam path toward the target mixture 1014. The target material of the targets 118, 318 and the modified target 319 may be or include the target mixture 1014. The target region 1005 is within an interior 1007 of a vacuum chamber 1030. When the amplified light beam 1010 strikes the target mixture 1014, a target material within the target mixture 1014 is converted into a plasma state that has an element with an emission line in the EUV range. The created plasma has certain characteristics that depend on the composition of the target material within the target mixture 1014. These characteristics may include the wavelength of the EUV light produced by the plasma and the type and amount of debris released from the plasma.

The light source 1000 also includes a target material delivery system 1025 that delivers, controls, and directs the target mixture 1014 in the form of liquid droplets, a liquid stream, solid particles or clusters, solid particles contained within liquid droplets or solid particles contained within a liquid stream. The target mixture 1014 includes the target material such as, for example, water, tin, lithium, xenon, or any material that, when converted to a plasma state, has an emission line in the EUV range. For example, the element tin may be used as pure tin (Sn); as a tin compound, for example, $SnBr_4$, $SnBr_2$, $SnH_4$; as a tin alloy, for example, tin-gallium alloys, tin-indium alloys, tin-indium-gallium alloys, or any combination of these alloys. The target mixture 1014 may also include impurities such as non-target particles. Thus, in the situation in which there are no impurities, the target mixture 1014 is made up of only the target material. The target mixture 1014 is delivered by the target material delivery system 1025 into the interior 1007 of the chamber 1030 and to the target region 1005.

The light source 1000 includes a drive laser system 1015 that produces the amplified light beam 1010 due to a population inversion within the gain medium or mediums of the laser system 1015. The light source 1000 includes a beam delivery system between the laser system 1015 and the target region 1005, the beam delivery system including a beam transport system 1020 and a focus assembly 1022. The beam transport system 1020 receives the amplified light beam 1010 from the laser system 1015, and steers and modifies the amplified light beam 1010 as needed and outputs the amplified light beam 1010 to the focus assembly 1022. The focus assembly 1022 receives the amplified light beam 1010 and focuses the beam 1010 to the target region 1005.

In some implementations, the laser system 1015 may include one or more optical amplifiers, lasers, and/or lamps for providing one or more main pulses and, in some cases, one or more pre-pulses. Each optical amplifier includes a gain medium capable of optically amplifying the desired wavelength at a high gain, an excitation source, and internal optics. The optical amplifier may or may not have laser mirrors or other feedback devices that form a laser cavity. Thus, the laser system 1015 produces an amplified light beam 1010 due to the population inversion in the gain media of the laser amplifiers even if there is no laser cavity. Moreover, the laser system 1015 may produce an amplified light beam 1010 that is a coherent laser beam if there is a laser cavity to provide enough feedback to the laser system 1015. The term "amplified light beam" encompasses one or more of: light from the laser system 1015 that is merely amplified but not necessarily a coherent laser oscillation and light from the laser system 1015 that is amplified and is also a coherent laser oscillation.

The optical amplifiers in the laser system 1015 may include as a gain medium a filling gas that includes $CO_2$ and may amplify light at a wavelength of between about 9100 and about 11000 nm, and in particular, at about 10600 nm, at a gain greater than or equal to 800. Suitable amplifiers and lasers for use in the laser system 1015 may include a pulsed laser device, for example, a pulsed, gas-discharge $CO_2$ laser device producing radiation at about 9300 nm or about 10600 nm, for example, with DC or RF excitation, operating at relatively high power, for example, 10 kW or higher and high pulse repetition rate, for example, 40 kHz or more. The optical amplifiers in the laser system 1015 may also include a cooling system such as water that may be used when operating the laser system 1015 at higher powers.

FIG. 10B shows a block diagram of a drive laser system 1080. The drive laser system 1080 may be used as part of the drive laser system 1015 in the source 1000. The drive laser system 1080 includes three power amplifiers 1081, 1082, and 1083. Any or all of the power amplifiers 1081, 1082, and 1083 may include internal optical elements (not shown).

Light 1084 exits the power amplifier 1081 through an output window 1085 and is reflected off a curved mirror 1086. After reflection, the light 1084 passes through a spatial filter 1087, is reflected off of a curved mirror 1088, and enters the power amplifier 1082 through an input window 1089. The light 1084 is amplified in the power amplifier 1082 and redirected out of the power amplifier 1082 through an output window 1090 as light 1091. The light 1091 is directed toward the amplifier 1083 with a fold mirror 1092 and enters the amplifier 1083 through an input window 1093. The amplifier 1083 amplifies the light 1091 and directs the light 1091 out of the amplifier 1083 through an output window 1094 as an output beam 1095. A fold mirror 1096 directs the output beam 1095 upward (out of the page) and toward the beam transport system 1020 (FIG. 10A).

The spatial filter 1087 defines an aperture 1097, which may be, for example, a circle having a diameter between about 2.2 mm and 3 mm. The curved mirrors 1086 and 1088 may be, for example, off-axis parabola mirrors with focal lengths of about 1.7 m and 2.3 m, respectively. The spatial filter 1087 may be positioned such that the aperture 1097 coincides with a focal point of the drive laser system 1080.

Referring again to FIG. 10A, the light source 1000 includes a collector mirror 1035 having an aperture 1040 to allow the amplified light beam 1010 to pass through and reach the target region 1005. The collector mirror 1035 may be, for example, an ellipsoidal mirror that has a primary focus at the target region 1005 and a secondary focus at an intermediate location 1045 (also called an intermediate focus) where the EUV light may be output from the light source 1000 and may be input to, for example, an integrated circuit lithography tool (not shown). The light source 1000 may also include an open-ended, hollow conical shroud 1050 (for example, a gas cone) that tapers toward the target region 1005 from the collector mirror 1035 to reduce the amount of plasma-generated debris that enters the focus assembly 1022 and/or the beam transport system 1020 while allowing the amplified light beam 1010 to reach the target region 1005. For this purpose, a gas flow may be provided in the shroud that is directed toward the target region 1005.

The light source 1000 may also include a master controller 1055 that is connected to a droplet position detection feedback system 1056, a laser control system 1057, and a beam control system 1058. The light source 1000 may include one or more target or droplet imagers 1060 that provide an output indicative of the position of a droplet, for example, relative to the target region 1005 and provide this output to the droplet position detection feedback system 1056, which may, for example, compute a droplet position and trajectory from which a droplet position error may be computed either on a droplet by droplet basis or on average. The droplet position detection feedback system 1056 thus provides the droplet position error as an input to the master controller 1055. The master controller 1055 may therefore provide a laser position, direction, and timing correction signal, for example, to the laser control system 1057 that may be used, for example, to control the laser timing circuit and/or to the beam control system 1058 to control an amplified light beam position and shaping of the beam transport system 1020 to change the location and/or focal power of the beam focal spot within the chamber 1030.

The target material delivery system 1025 includes a target material delivery control system 1026 that is operable, in response to a signal from the master controller 1055, for example, to modify the release point of the droplets as released by a target material supply apparatus 1027 to correct for errors in the droplets arriving at the desired target region 1005.

Additionally, the light source 1000 may include light source detectors 1065 and 1070 that measures one or more EUV light parameters, including but not limited to, pulse energy, energy distribution as a function of wavelength, energy within a particular band of wavelengths, energy outside of a particular band of wavelengths, and angular distribution of EUV intensity and/or average power. The light source detector 1065 generates a feedback signal for use by the master controller 1055. The feedback signal may be, for example, indicative of the errors in parameters such as the timing and focus of the laser pulses to properly intercept the droplets in the right place and time for effective and efficient EUV light production.

The light source 1000 may also include a guide laser 1075 that may be used to align various sections of the light source 1000 or to assist in steering the amplified light beam 1010 to the target region 1005. In connection with the guide laser 1075, the light source 1000 includes a metrology system 1024 that is placed within the focus assembly 1022 to sample a portion of light from the guide laser 1075 and the amplified light beam 1010. In other implementations, the metrology system 1024 is placed within the beam transport system 1020. The metrology system 1024 may include an optical element that samples or re-directs a subset of the light, such optical element being made out of any material that may withstand the powers of the guide laser beam and the amplified light beam 1010. A beam analysis system is formed from the metrology system 1024 and the master controller 1055 since the master controller 1055 analyzes the sampled light from the guide laser 1075 and uses this information to adjust components within the focus assembly 1022 through the beam control system 1058.

Thus, in summary, the light source 1000 produces an amplified light beam 1010 that is directed along the beam path to irradiate the target mixture 1014 at the target region 1005 to convert the target material within the mixture 1014 into plasma that emits light in the EUV range. The amplified light beam 1010 operates at a particular wavelength (that is also referred to as a drive laser wavelength) that is determined based on the design and properties of the laser system 1015. Additionally, the amplified light beam 1010 may be a laser beam when the target material provides enough feedback back into the laser system 1015 to produce coherent laser light or if the drive laser system 1015 includes suitable optical feedback to form a laser cavity.

Other implementations are within the scope of the claims. For example, the detection system 460A (FIG. 4A) may include more than two beam dividers such that the reflection 314 and the detection light 313 and 314 may be further divided and directed into additional sensors. The particular polarization states discussed with respect to FIG. 3A are provided as examples, and the light beam 306a, the metrology light beam 208, and the reflection 214 may have other polarization states. In some implementations, the second light beam 306b may be directed along the same path as the metrology light beam 308 or 508 and the first light beam 306a (for example, path 311 or the path 511).

What is claimed is:

1. A system for an EUV light source, the system comprising:
   a metrology light source configured to emit a metrology light beam; and
   an optical beam combiner configured to be positioned to receive the metrology light beam and at least one other light beam and to direct the metrology light beam and the at least one other light beam onto a beam path toward a target region configured to receive a target, wherein
   after interacting with the optical beam combiner, the metrology light beam and the at least one other light beam have the same polarization state, and
   the metrology light beam is configured to reflect from the target without changing a property of the target and the at least one other light beam is configured to change a property of the target.

2. The system of claim 1, wherein the optical beam combiner comprises a polarizing beam splitter, and an optical modulator, and the system for the EUV light source further comprises a control system coupled to the optical modulator, the control system configured to control the optical modulator such that the metrology light beam and the at least one other light beam have the same polarization state after passing through the optical modulator toward the target region.

3. The system of claim 2, wherein the metrology light beam and the at least one other light beam comprise substantially the same spectral content, and the metrology light beam and the at least one other light beam have different polarization states prior to passing through the optical modulator of the optical beam combiner.

4. The system of claim 1, wherein
the at least one other light beam comprises a first light beam,
the metrology light beam has a first spectral content, and the first light beam has a second spectral content, the first spectral content comprising at least a first wavelength and the second spectral content comprising at least a second wavelength, the first and second wavelengths being different wavelengths, and
the optical beam combiner comprises a dichroic optical element, the dichroic optical element configured to transmit light having one of the first wavelength and the second wavelength and to reflect light having the other of the first wavelength and the second wavelength.

5. The system of claim 3, further comprising a second optical element, the second optical element being between the optical modulator and the target region, and wherein the second optical element is configured to direct a reflection of the metrology light beam and a reflection of the at least one other beam onto a detection beam path.

6. The system of claim 5, further comprising one or more sensors, each sensor configured to be positioned to receive a portion of a light beam that propagates on the detection beam path.

7. The system of claim 6, wherein the at least one other light beam comprises a first light beam, and the system further comprises:
a polarization-based optical isolator configured to be positioned on the detection beam path between at least one of the one or more sensors and the second optical element, the polarization-based optical isolator comprising:
a second optical modulator coupled to the control system; and
a third optical element configured to interact with incident light based on a polarization state of the incident light, wherein
the optical modulator of the polarization-based optical isolator is configured to be controlled such that, after passing through the optical modulator,
a polarization state of a reflection of the metrology light beam and a polarization state of a reflection of the first light beam are different.

8. The system of claim 7, wherein:
the optical modulator and the second optical modulator each comprise an electro-optic modulator; and
the second optical element and the third optical element each comprise a polarizing beam splitter, the third optical element being configured to be positioned to deflect a reflection of the first light beam away from the detection beam path.

9. The system of claim 1, further comprising a beam conditioning module between the metrology light source and the optical beam combiner, the beam conditioning module comprising one or more optical elements configured to increase a beam diameter of the metrology light beam.

10. The system of claim 1, wherein the target comprises an initial target, and the at least one other light beam is a first light beam having an energy sufficient to modify a geometric distribution of target material in the initial target that interacts with the first light beam.

11. The system of claim 6, wherein the one or more sensors comprise a first sensor configured to accumulate light over a first time period and a second sensor configured to monitor changes in an amount of light received at instances within the first time period.

12. The system of claim 11, wherein the first sensor comprises a camera and the second sensor comprises a photodiode.

13. The system of claim 1, wherein the metrology light source is configured to emit a continuous wave light beam.

14. The system of claim 1, wherein the metrology light source is controllable to emit either a pulsed light beam or a continuous wave light beam.

15. A method for an EUV light source, the method comprising:
directing a metrology light beam onto a beam path toward an initial target region configured to receive a target, wherein:
the metrology light beam has a wavelength and a polarization state, and
the target comprises target material, the target material comprising material that reflects light having the wavelength of the metrology light beam and emits EUV light when in a plasma state;
directing a first light beam onto the beam path toward the initial target region, the first light beam and the metrology light beam having substantially the same polarization state, and the first light beam having an energy sufficient to alter a geometric distribution of target material in the target to form a modified target;
directing a second light beam toward a modified target region that receives the modified target, the second light beam having an energy sufficient to convert at least some of the target material in the modified target to plasma that emits EUV light; and
receiving a reflection of the metrology light beam, and wherein the first light beam is directed onto the beam path toward the initial target region based on the received reflection of the metrology light beam.

16. The method of claim 15, wherein the first light beam is generated by a first light source, and the first light beam being directed on the beam path toward the initial target region based on the received reflection comprises the first light source being controlled to emit the first light beam only after the reflection of the metrology light beam is received.

17. The method of claim 15, wherein:
directing the metrology light beam onto the beam path toward the initial target region comprises passing the metrology light beam through an electro-optic modulator,
directing the first light beam onto the beam path toward the initial target region comprises passing the first light beam through the electro-optic modulator, and
the electro-optic modulator is controlled such that, after passing through the electro-optic modulator, the metrology light beam and the first light beam have the same polarization state.

18. The method of claim 17, wherein, prior to directing the metrology light beam and the first light beam onto the beam path, a direction of propagation of at least one of the metrology light beam and the first light beam is changed such that both the metrology light beam and the first light beam propagate toward the initial target region.

19. The method of claim 18, wherein the direction of propagation of the at least one of the metrology light beam and the first light beam is changed through interaction with a polarizing beam splitter.

20. The method of claim 17, wherein, prior to passing through the electro-optic modulator, the metrology light beam and the first light beam have different polarization states.

21. The method of claim 15, wherein a beam diameter of the metrology light beam directed toward the initial target region is larger than a beam diameter of the first light beam directed toward the initial target region.

22. The method of claim 21, further comprising interacting the metrology light beam with a beam conditioning system prior to directing the metrology light beam toward the initial target region, the beam conditioning system expanding a diameter of the metrology light beam to at least the diameter of the initial target region.

23. The method of claim 15, wherein the metrology light beam directed on the beam path and the first light beam directed on the beam path have substantially the same spectral content.

24. A method comprising:
receiving, at an imaging device, light associated with a metrology light beam from an interior of a vacuum chamber of an EUV light source;
receiving, at the imaging device, light associated with a first light beam from the interior of the vacuum chamber, wherein:
the first light beam has an energy sufficient to modify a geometric distribution of target material in a target in the vacuum chamber, and
the light associated with the first light beam is received at a different portion of the imaging device than the light associated with the metrology light beam and at a different time than the light associated with the metrology light beam; and
generating a representation of the metrology light beam and the first light beam in the vacuum chamber based on the received light associated with the metrology light beam and the received light associated with the first light beam, the representation comprising two-dimensional spatial information related to the metrology light beam and the first light beam in the vacuum chamber.

25. The method of claim 24, further comprising:
receiving, at the imaging device, light associated with a second light beam from the vacuum chamber, the second light beam having an energy sufficient to convert target material to EUV light when in a plasma state, and wherein:
the representation further comprises a representation of the second light beam in the vacuum chamber based on the received light associated with the second light beam, and the representation further comprises two-dimensional spatial information related to the second light beam in the vacuum chamber.

26. The method of claim 25, wherein:
the light associated with the metrology light beam comprises a reflection of the metrology light beam from target material in the vacuum chamber,
the light associated with the first light beam comprises a reflection of the first light beam from the target material in the vacuum chamber, and the light associated with the second light beam comprises non-EUV light emitted by a plasma formed by an interaction between the second light beam and the target material in the vacuum chamber.

27. The method of claim 26, further comprising:
receiving the light associated with the metrology light beam at the imaging device at a first time;
receiving the light associated with the first light beam at the imaging device at a second time;
receiving the light associated with the second light beam at the imaging device at a third time; and
determining spatial coordinates for the representation of the metrology light beam, the representation of the first light beam, and the representation of the second light beam based on the first time, the second time, and the third time, respectively.

28. The method of claim 27, wherein the spatial coordinates represent a location in the vacuum chamber in a first dimension and a second dimension, the first dimension being along a direction that is parallel to a direction in which target material is introduced into the vacuum chamber, and the second dimension being orthogonal to the first dimension.

29. The method of claim 26, further comprising analyzing the representation to determine an estimated value of one or more properties of the first light beam in the vacuum chamber.

30. The method of claim 25, further comprising visually presenting the generated representation, the presented representation comprising a first display style associated with the metrology light beam, a second display style associated with the first light beam, and a third display style associated with the second light beam, wherein
the first display style, the second display style, and the third display style are visually distinguishable from each other.

31. The system of claim 1, wherein the at least one other light beam is a light beam having an energy sufficient to convert at least some target material in the target to a plasma that emits EUV light.

32. The system of claim 1, wherein the at least one other light beam comprises a first light beam having an energy sufficient to modify a geometric distribution of target material in an initial target that interacts with the first light beam to form a modified target, and a second light beam having an energy sufficient to convert at least some of the target material in the modified target to a plasma that emits EUV light.

33. A system for an EUV light source, the system comprising:
a metrology light source configured to emit a metrology light beam; and
an optical beam combiner configured to be positioned to receive the metrology light beam and at least one other light beam and to direct the metrology light beam and the at least one other light beam onto a beam path toward a target region, wherein
after interacting with the optical beam combiner, the metrology light beam and the at least one other light beam have the same polarization state, wherein
the optical beam combiner comprises a polarizing beam splitter, and an optical modulator, and the system for the EUV light source further comprises a control system coupled to the optical modulator, the control system configured to control the optical modulator such that the metrology light beam and the at least one other light beam have the same polarization state after passing through the optical modulator toward the target region.

34. The system of claim 33, wherein the metrology light beam and the at least one other light beam comprise substantially the same spectral content, and the metrology light beam and the at least one other light beam have different polarization states prior to passing through the optical modulator of the optical beam combiner.

* * * * *